United States Patent
McIntyre et al.

(10) Patent No.: US 11,351,332 B2
(45) Date of Patent: Jun. 7, 2022

(54) SENSING ARRANGEMENTS FOR MEDICAL DEVICES

(71) Applicant: Fisher & Paykel Healthcare Limited, Auckland (NZ)

(72) Inventors: Joshua Peter McIntyre, Auckland (NZ); Matthew Michael Marinovich, Auckland (NZ); Hamish Adrian Osborne, Auckland (NZ); Graeme Matthew Smith, Auckland (NZ); Benjamin John Ingram, Auckland (NZ); Samuel Graham Boggs, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 378 days.

(21) Appl. No.: 16/466,263

(22) PCT Filed: Dec. 7, 2017

(86) PCT No.: PCT/NZ2017/050157
§ 371 (c)(1),
(2) Date: Jun. 3, 2019

(87) PCT Pub. No.: WO2018/106126
PCT Pub. Date: Jun. 14, 2018

(65) Prior Publication Data
US 2020/0061329 A1    Feb. 27, 2020

Related U.S. Application Data

(60) Provisional application No. 62/431,372, filed on Dec. 7, 2016.

(51) Int. Cl.
*A61M 16/16*    (2006.01)
*A61M 16/10*    (2006.01)
*A61M 16/00*    (2006.01)

(52) U.S. Cl.
CPC .......... *A61M 16/16* (2013.01); *A61M 16/109* (2014.02); *A61M 2016/003* (2013.01);
(Continued)

(58) Field of Classification Search
CPC .............. A61M 16/00; A61M 16/0003; A61M 16/0841; A61M 16/085; A61M 16/16;
(Continued)

(56) References Cited

U.S. PATENT DOCUMENTS

| 1,085,833 A | 2/1914 | Wilson |
| 1,154,259 A | 9/1915 | Light |

(Continued)

FOREIGN PATENT DOCUMENTS

| AU | 667538 | 3/1996 |
| AU | 726022 | 10/2000 |

(Continued)

OTHER PUBLICATIONS

International Search Report, PCT/NZ2014/000201; dated Jan. 13, 2015; 20 pages.

(Continued)

*Primary Examiner* — Joseph D. Boecker
(74) *Attorney, Agent, or Firm* — Knobbe Martens Olson & Bear, LLP

(57) ABSTRACT

A sensing arrangement for a medical device includes a housing having a rigid portion and a flexible portion, a collar of the flexible portion attached to an exterior of the rigid portion such that a stem of the rigid portion extends into an interior of the flexible portion. A sensing element is positioned at least partially within a passageway of the rigid portion, with at least one wire extending from the sensing element through the passageway and into the interior of the flexible portion. Front and rear flanges protrude from the flexible portion and are adapted to allow the sensing (Continued)

arrangement to be attached into an aperture in a wall of the medical device. The stem of the rigid portion may be positioned between the collar and front flanges of the flexible portion, such that the stem does not extend through the aperture of the wall of the medical device. There are also provided a seal, a removable component, a medical device and a system.

23 Claims, 7 Drawing Sheets

(52) U.S. Cl.
CPC ............... *A61M 2016/0027* (2013.01); *A61M 2016/102* (2013.01); *A61M 2202/025* (2013.01); *A61M 2202/0208* (2013.01); *A61M 2202/0225* (2013.01); *A61M 2202/0275* (2013.01); *A61M 2205/3324* (2013.01); *A61M 2205/3368* (2013.01); *A61M 2205/3375* (2013.01)

(58) Field of Classification Search
CPC .. A61M 2016/0018; A61M 2016/0021; A61M 2016/0024; A61M 2016/0027; A61M 2016/003; A61M 2016/0033; A61M 2016/0036; A61M 2016/0039; G01K 1/08; G01K 1/14; G01K 13/024
See application file for complete search history.

(56) References Cited

U.S. PATENT DOCUMENTS

| | | | |
|---|---|---|---|
| 2,073,335 A | 3/1937 | Connell |
| 2,510,125 A | 6/1950 | Meakin |
| 2,516,864 A | 8/1950 | Gilmore et al. |
| 2,745,074 A | 1/1951 | Darling |
| 2,590,797 A | 3/1952 | Siciliano |
| 2,621,875 A | 12/1952 | Darling |
| 2,634,311 A | 4/1953 | Darling |
| 3,117,596 A | 1/1964 | Kahn |
| 3,163,707 A | 12/1964 | Darling |
| 3,283,580 A | 11/1966 | Jacob et al. |
| 3,394,954 A | 7/1968 | Sarns |
| 3,404,684 A | 10/1968 | Brewer et al. |
| 3,485,237 A | 12/1969 | Bedford |
| 3,495,628 A | 2/1970 | Boender |
| 3,582,094 A | 6/1971 | Whittaker |
| 3,588,859 A | 6/1971 | Petree |
| 3,623,511 A | 11/1971 | Levin |
| 3,638,926 A | 2/1972 | Melville et al. |
| 3,659,604 A | 5/1972 | Melville et al. |
| 3,703,892 A | 11/1972 | Meyers |
| 3,777,298 A | 12/1973 | Newman |
| 3,806,102 A | 4/1974 | Valenta et al. |
| 3,903,742 A | 9/1975 | Colton |
| 3,945,378 A | 3/1976 | Paluch |
| 3,954,920 A | 5/1976 | Heath |
| 3,987,133 A | 10/1976 | Andra |
| 3,990,727 A | 11/1976 | Gallagher |
| 4,010,748 A | 3/1977 | Dobritz |
| 4,028,444 A | 6/1977 | Brown |
| 4,038,519 A | 7/1977 | Foucras |
| 4,060,576 A | 11/1977 | Grant |
| 4,098,853 A | 7/1978 | Brown et al. |
| 4,111,197 A | 9/1978 | Warncke et al. |
| 4,139,762 A | 2/1979 | Pohrer et al. |
| 4,152,379 A | 5/1979 | Suhr |
| 4,160,466 A | 7/1979 | Jousson |
| 4,172,709 A | 10/1979 | Kippel et al. |
| 4,183,248 A | 1/1980 | West |
| 4,192,836 A | 3/1980 | Bartscher |
| 4,301,200 A | 11/1981 | Langenfeld et al. |
| 4,333,451 A | 6/1982 | Paluch |
| 4,417,574 A | 11/1983 | Taloon et al. |
| 4,428,403 A | 1/1984 | Lee et al. |
| 4,463,593 A | 8/1984 | Parker |
| 4,473,923 A | 10/1984 | Neroni et al. |
| 4,529,867 A | 7/1985 | Velnosky et al. |
| 4,531,551 A | 7/1985 | Eichelberger et al. |
| 4,533,115 A | 8/1985 | Lissau |
| 4,545,290 A | 10/1985 | Lieberman |
| 4,558,708 A | 12/1985 | Labuda et al. |
| 4,564,748 A | 1/1986 | Gupton |
| 4,588,425 A | 5/1986 | Usry et al. |
| 4,599,895 A | 7/1986 | Wiseman |
| 4,621,632 A | 11/1986 | Bartels et al. |
| 4,676,237 A | 6/1987 | Wood et al. |
| 4,686,354 A | 8/1987 | Makin |
| 4,708,831 A | 11/1987 | Elsworth et al. |
| 4,714,078 A | 12/1987 | Paluch |
| 4,753,758 A | 6/1988 | Miller |
| 4,774,032 A | 9/1988 | Coates et al. |
| 4,809,698 A | 3/1989 | Kogo |
| 4,813,280 A | 3/1989 | Miller, Jr. et al. |
| 4,830,515 A | 5/1989 | Cortes |
| 4,844,512 A | 7/1989 | Gahwiler |
| 4,942,877 A | 7/1990 | Sakai et al. |
| 4,944,310 A | 7/1990 | Sullivan |
| 4,967,744 A | 11/1990 | Chua |
| 5,017,875 A | 5/1991 | Hori |
| 5,027,811 A | 7/1991 | Tuxill |
| 5,031,612 A | 7/1991 | Clementi |
| 5,038,773 A | 8/1991 | Norlien |
| 5,054,819 A | 10/1991 | Grunwald |
| 5,058,588 A | 10/1991 | Kaestle |
| 5,060,506 A | 10/1991 | Douglas |
| 5,062,145 A | 10/1991 | Zwaan |
| 5,117,819 A | 6/1992 | Servidio et al. |
| 5,127,442 A | 7/1992 | Blomqvist |
| 5,134,996 A | 8/1992 | Bell |
| 5,143,060 A | 9/1992 | Smith |
| 5,148,801 A | 9/1992 | Douwens et al. |
| 5,181,858 A | 1/1993 | Matz et al. |
| 5,209,225 A | 5/1993 | Glenn |
| 5,213,138 A | 5/1993 | Presz, Jr. |
| 5,213,376 A | 5/1993 | Szabo |
| 5,233,996 A | 8/1993 | Coleman et al. |
| 5,303,701 A | 4/1994 | Heins et al. |
| RE34,599 E | 5/1994 | Suszynk et al. |
| 5,342,126 A | 8/1994 | Heston et al. |
| 5,357,948 A | 10/1994 | Eilentropp |
| 5,367,604 A | 11/1994 | Murray |
| 5,392,770 A | 2/1995 | Clawson et al. |
| 5,396,884 A | 3/1995 | Bagwell et al. |
| 5,454,061 A | 9/1995 | Carlson |
| 5,454,479 A | 10/1995 | Kraus |
| 5,483,616 A | 1/1996 | Chiu et al. |
| 5,484,223 A | 1/1996 | Saito |
| 5,488,447 A | 1/1996 | Patton et al. |
| 5,495,872 A | 3/1996 | Gallagher et al. |
| 5,499,737 A | 3/1996 | Kraus |
| RE35,225 E | 4/1996 | Herweck et al. |
| 5,529,093 A | 6/1996 | Gallagher et al. |
| 5,537,996 A | 7/1996 | McPhee |
| 5,540,219 A | 7/1996 | Mechlenburg et al. |
| 5,548,879 A | 8/1996 | Wu |
| 5,551,883 A | 9/1996 | Davis |
| 5,558,084 A | 9/1996 | Daniell et al. |
| 5,564,415 A | 10/1996 | Dobson et al. |
| 5,598,837 A | 2/1997 | Sirianne et al. |
| 5,600,752 A | 2/1997 | Lopatinsky |
| 5,630,806 A | 5/1997 | Inagaki et al. |
| 5,637,006 A | 6/1997 | Almeras |
| 5,640,951 A | 6/1997 | Huddart et al. |
| 5,660,567 A | 8/1997 | Nierlich et al. |
| 5,667,306 A | 9/1997 | Montreuil et al. |
| 5,720,293 A | 2/1998 | Quinn et al. |
| 5,778,872 A | 7/1998 | Fukunaga et al. |
| 5,829,880 A | 11/1998 | Diedrich |
| 5,881,393 A | 3/1999 | Marchello |
| 5,906,201 A | 5/1999 | Nilson |
| 5,913,249 A | 6/1999 | Weckstrom |

(56) References Cited

U.S. PATENT DOCUMENTS

| | | |
|---|---|---|
| 5,943,473 A | 8/1999 | Levine |
| 5,975,591 A | 11/1999 | Guest |
| 5,979,247 A | 11/1999 | Kizawa |
| D419,522 S | 1/2000 | Kamagai |
| 6,024,694 A | 2/2000 | Goldberg |
| 6,039,696 A | 3/2000 | Bell |
| 6,050,260 A | 4/2000 | Daniell |
| 6,053,482 A | 4/2000 | Glenn et al. |
| 6,058,977 A | 5/2000 | Hotta |
| 6,078,729 A | 6/2000 | Kopel |
| 6,078,730 A | 6/2000 | Huddart et al. |
| 6,095,505 A | 8/2000 | Miller |
| 6,102,037 A | 8/2000 | Koch |
| 6,105,970 A | 8/2000 | Siegrist et al. |
| 6,126,610 A | 10/2000 | Rich et al. |
| 6,128,963 A | 10/2000 | Bromster |
| 6,138,674 A | 10/2000 | Gull et al. |
| 6,190,480 B1 | 2/2001 | Carlson |
| 6,196,980 B1 | 3/2001 | Akerfeldt et al. |
| 6,201,983 B1 | 3/2001 | Haumann et al. |
| 6,208,514 B1 | 3/2001 | Stark |
| 6,226,451 B1 | 5/2001 | Wong |
| 6,272,933 B1 | 8/2001 | Gradon et al. |
| 6,332,462 B1 | 12/2001 | Krohn |
| 6,347,646 B2 | 2/2002 | Fukui et al. |
| 6,349,722 B1 | 2/2002 | Gradon et al. |
| 6,349,724 B1 | 2/2002 | Burton et al. |
| 6,360,741 B2 | 3/2002 | Truschel |
| 6,367,974 B1 | 4/2002 | Lin |
| 6,374,864 B1 | 4/2002 | Philp |
| 6,394,145 B1 | 5/2002 | Gessil |
| 6,397,841 B1 | 6/2002 | Kenyon et al. |
| 6,402,207 B1 | 6/2002 | Segal et al. |
| 6,435,180 B1 | 8/2002 | Hewson et al. |
| 6,467,477 B1 | 10/2002 | Frank et al. |
| 6,508,249 B2 | 1/2003 | Hoenig |
| 6,511,075 B1 | 1/2003 | Schmidt |
| 6,540,734 B1 | 4/2003 | Chiu et al. |
| 6,551,143 B2 | 4/2003 | Tanaka et al. |
| 6,554,260 B1 | 4/2003 | Lipscombe et al. |
| 6,591,061 B2 | 7/2003 | Wang |
| 6,598,604 B1 | 7/2003 | Seakins |
| 6,600,727 B1 | 7/2003 | Mackay |
| 6,612,624 B1 | 9/2003 | Segal et al. |
| 6,623,352 B2 | 9/2003 | Illingworth |
| 6,631,718 B1 | 10/2003 | Lovell |
| 6,648,669 B1 | 11/2003 | Kim et al. |
| 6,655,207 B1 | 12/2003 | Speldrich et al. |
| 6,668,828 B1 | 12/2003 | Figley et al. |
| 6,685,491 B2 | 2/2004 | Gergek |
| 6,698,966 B2 | 3/2004 | Hilton et al. |
| 6,824,180 B2 | 11/2004 | Tomchak |
| 6,827,084 B2 | 12/2004 | Grubb, Jr. |
| 6,874,771 B2 | 4/2005 | Birdsell et al. |
| 6,895,803 B2 | 5/2005 | Seakins et al. |
| 6,915,705 B1 | 7/2005 | Truitt et al. |
| 6,918,389 B2 | 7/2005 | Seakins et al. |
| 6,935,337 B2 | 8/2005 | Virr et al. |
| 6,943,566 B2 | 9/2005 | Florin et al. |
| 6,953,354 B2 | 10/2005 | Edirisuriya et al. |
| 7,043,979 B2 | 5/2006 | Smith et al. |
| 7,063,668 B2 | 6/2006 | Cardeli et al. |
| 7,086,422 B2 | 8/2006 | Huber et al. |
| 7,090,541 B1 | 8/2006 | Ho |
| 7,096,864 B1 | 8/2006 | Mayer et al. |
| 7,120,354 B2 | 10/2006 | Mackie et al. |
| 7,137,654 B2 | 11/2006 | Segal et al. |
| 7,140,367 B2 | 11/2006 | White et al. |
| 7,157,035 B2 | 1/2007 | Edirisuriya et al. |
| 7,191,780 B2 | 3/2007 | Faram |
| 7,225,809 B1 | 6/2007 | Bowen et al. |
| 7,284,554 B2 | 10/2007 | Shaw |
| 7,316,768 B2 | 1/2008 | Aldridge et al. |
| 7,327,547 B1 | 2/2008 | Epstein |
| 7,327,949 B1 | 2/2008 | Cheng et al. |
| 7,334,587 B2 | 2/2008 | Lake |
| 7,364,436 B2 | 4/2008 | Yen |
| 7,396,995 B2 | 7/2008 | Laurent et al. |
| 7,448,383 B2 | 11/2008 | Delache et al. |
| 7,469,586 B2 | 12/2008 | Wild et al. |
| 7,478,635 B2 | 1/2009 | Wixey et al. |
| 7,525,663 B2 | 4/2009 | Kwok et al. |
| 7,607,360 B2 | 10/2009 | Todokoro et al. |
| 7,614,398 B2 | 11/2009 | Virr et al. |
| 7,637,288 B2 | 12/2009 | Kressierer/Huber et al. |
| 7,677,246 B2 | 3/2010 | Kepler et al. |
| 7,743,767 B2 | 6/2010 | Ging et al. |
| 7,766,050 B2 | 8/2010 | Patel |
| 7,794,426 B2 | 9/2010 | Briones et al. |
| 7,814,907 B2 | 10/2010 | Bremner et al. |
| 7,816,888 B2 | 10/2010 | Rejman et al. |
| D628,288 S | 11/2010 | Row et al. |
| 7,827,981 B2 | 11/2010 | Barnford |
| 7,870,857 B2 | 1/2011 | Dhuper et al. |
| 7,874,291 B2 | 1/2011 | Ging et al. |
| 7,900,528 B2 | 3/2011 | Vincent |
| 7,913,689 B2 | 3/2011 | Henry et al. |
| 7,942,380 B2 | 5/2011 | Bertinetti et al. |
| 7,942,389 B2 | 5/2011 | Koch et al. |
| 7,965,930 B2 | 6/2011 | Carlson et al. |
| 7,983,542 B2 | 7/2011 | McGhin et al. |
| 7,987,847 B2 | 8/2011 | Wickham |
| 7,992,554 B2 | 8/2011 | Radomski et al. |
| 7,997,267 B2 | 8/2011 | Ging et al. |
| 8,025,849 B2 | 9/2011 | Baldwin et al. |
| 8,059,947 B2 | 11/2011 | Bradley et al. |
| 8,063,343 B2 | 11/2011 | McGhin et al. |
| 8,078,040 B2 | 12/2011 | Forrester |
| 8,100,124 B2 | 1/2012 | Becker et al. |
| 8,122,882 B2 | 2/2012 | McGhin et al. |
| 8,136,521 B2 | 3/2012 | Matthews et al. |
| 8,137,082 B2 | 3/2012 | Campbell |
| 8,181,940 B2 | 5/2012 | Payne et al. |
| 8,182,144 B2 | 5/2012 | Koch |
| 8,186,345 B2 | 5/2012 | Payton et al. |
| 8,186,352 B2 | 5/2012 | Gunaratnam et al. |
| 8,197,123 B2 | 6/2012 | Snyder et al. |
| 8,206,337 B2 | 6/2012 | Blackhurst et al. |
| 8,221,530 B2 | 7/2012 | Peter et al. |
| 8,240,306 B2 | 8/2012 | Cortez, Jr. et al. |
| 8,245,709 B2 | 8/2012 | Rossen et al. |
| 8,245,710 B2 | 8/2012 | Makinson et al. |
| 8,253,076 B2 | 8/2012 | Andel et al. |
| 8,257,286 B2 | 9/2012 | Meyer et al. |
| 8,267,084 B2 | 9/2012 | Kwok |
| 8,267,614 B2 | 9/2012 | Khoe |
| 8,282,427 B2 | 10/2012 | Yamazaki |
| 8,287,517 B2 | 10/2012 | Hanlon et al. |
| 8,316,848 B2 | 11/2012 | Kwok et al. |
| 8,333,194 B2 | 12/2012 | Lewis et al. |
| 8,333,195 B2 | 12/2012 | Cortez, Jr. et al. |
| 8,333,199 B2 | 12/2012 | Landis et al. |
| 8,355,753 B2 | 1/2013 | Bochenko et al. |
| 8,360,059 B2 | 1/2013 | Koulechov et al. |
| 8,365,726 B2 | 2/2013 | Snow et al. |
| 8,381,724 B2 | 2/2013 | Bowen et al. |
| 8,424,514 B2 | 4/2013 | Oates et al. |
| 8,453,641 B2 | 6/2013 | Payton et al. |
| 8,453,643 B2 | 6/2013 | Sanchez et al. |
| 8,459,261 B2 | 6/2013 | Ricciardelli |
| 8,469,025 B2 | 6/2013 | Mayer et al. |
| 8,490,621 B2 | 7/2013 | Radomski et al. |
| 8,496,001 B2 | 7/2013 | Schermeier et al. |
| RE44,453 E | 8/2013 | Virr et al. |
| 8,511,305 B2 | 8/2013 | Liu et al. |
| 8,511,651 B2 | 8/2013 | Fridberg et al. |
| 8,516,911 B2 | 8/2013 | Inoue et al. |
| 8,522,782 B2 | 9/2013 | Lewis et al. |
| 8,528,552 B2 | 9/2013 | von Blumenthal |
| 8,544,465 B2 | 10/2013 | Smith et al. |
| 8,545,096 B2 | 10/2013 | Reiter |
| 8,550,072 B2 | 10/2013 | Thudor et al. |
| 8,631,789 B2 | 1/2014 | Virr et al. |
| 8,640,696 B2 | 2/2014 | Pujol et al. |

(56) References Cited

U.S. PATENT DOCUMENTS

| | | |
|---|---|---|
| 8,651,800 B2 | 2/2014 | Li |
| 8,733,348 B2 | 5/2014 | Korneff et al. |
| 8,733,349 B2 | 5/2014 | Bath et al. |
| 8,756,990 B2 | 6/2014 | Speldrich |
| 8,776,790 B2 | 7/2014 | Gentner et al. |
| 8,783,252 B2 | 7/2014 | Pierro et al. |
| 8,800,970 B2 | 8/2014 | Heine et al. |
| 8,844,521 B2 | 9/2014 | McCarthy |
| 8,851,071 B2 | 10/2014 | Kuo et al. |
| 8,905,023 B2 | 12/2014 | Niland et al. |
| 8,915,250 B2 | 12/2014 | Dugan et al. |
| 8,931,481 B2 | 1/2015 | Jones et al. |
| 8,939,147 B2 | 1/2015 | Henry et al. |
| 8,985,105 B2 | 3/2015 | Burton et al. |
| 9,022,946 B2 | 5/2015 | Haque |
| 9,039,277 B2 | 5/2015 | Le Bouquin et al. |
| 9,067,036 B2 | 6/2015 | Korneff et al. |
| 9,095,668 B2 | 8/2015 | Blackhurst et al. |
| 9,119,933 B2 | 9/2015 | Bedford et al. |
| 9,132,252 B2 | 9/2015 | Barlow et al. |
| 9,162,035 B2 | 10/2015 | Kwok |
| 9,186,477 B2 | 11/2015 | Hunt et al. |
| 9,205,220 B2 | 12/2015 | Korneff et al. |
| 9,212,673 B2 | 12/2015 | Korneff et al. |
| 9,242,064 B2 | 1/2016 | Rustad et al. |
| 9,254,368 B2 | 2/2016 | Blumenthal et al. |
| 9,289,572 B2 | 3/2016 | Korneff et al. |
| RE46,079 E | 7/2016 | Virr et al. |
| 9,381,317 B2 | 7/2016 | Landis et al. |
| 9,387,299 B2 | 7/2016 | Zwolinsky et al. |
| 9,427,547 B2 | 8/2016 | Landis et al. |
| 9,446,210 B2 | 9/2016 | Orr et al. |
| 9,512,856 B2 | 12/2016 | Nibu |
| 9,517,321 B2 | 12/2016 | Buechi et al. |
| 9,545,493 B2 | 1/2017 | Mayer et al. |
| 9,566,409 B2 | 2/2017 | Gründler et al. |
| 9,572,949 B2 | 2/2017 | Vos et al. |
| 9,572,951 B2 | 2/2017 | Barker et al. |
| 9,586,019 B2 | 3/2017 | Heine et al. |
| 9,642,979 B2 | 5/2017 | Korneff et al. |
| RE46,571 E | 10/2017 | Virr et al. |
| 9,838,759 B2 | 12/2017 | Kirmse et al. |
| 9,861,778 B2 | 1/2018 | Roderick et al. |
| 9,937,314 B2 | 4/2018 | Buechi et al. |
| 9,937,316 B2 | 4/2018 | Buechi et al. |
| 9,974,921 B2 | 5/2018 | Klenner et al. |
| 9,987,455 B2 | 6/2018 | Stoks et al. |
| 10,046,136 B2 | 8/2018 | Pujol |
| 10,245,407 B2 | 4/2019 | Osborne et al. |
| 10,449,319 B2 | 10/2019 | Osborne et al. |
| 10,828,482 B2 | 11/2020 | Osborne et al. |
| 10,974,015 B2 | 4/2021 | Stoks et al. |
| 2001/0017134 A1 | 8/2001 | Bahr |
| 2001/0017880 A1 | 8/2001 | Beerwerth et al. |
| 2001/0050080 A1 | 12/2001 | Seakins et al. |
| 2002/0058436 A1 | 5/2002 | Saba |
| 2002/0100320 A1 | 8/2002 | Smith et al. |
| 2002/0132511 A1 | 9/2002 | Groebe et al. |
| 2002/0153011 A1 | 10/2002 | Tanhehco |
| 2003/0066526 A1 | 4/2003 | Thudor et al. |
| 2003/0066530 A1 | 4/2003 | Shahbazpour et al. |
| 2003/0107325 A1 | 6/2003 | Birkhead |
| 2003/0127096 A1 | 7/2003 | McAuliffe |
| 2003/0148664 A1 | 8/2003 | Cheng |
| 2003/0183294 A1 | 10/2003 | Carlson |
| 2003/0200727 A1 | 10/2003 | Kim |
| 2003/0236015 A1 | 12/2003 | Edirisuriya et al. |
| 2004/0013162 A1 | 1/2004 | Beerwerth et al. |
| 2004/0055597 A1 | 3/2004 | Virr et al. |
| 2004/0074493 A1 | 4/2004 | Seakins et al. |
| 2004/0079371 A1 | 4/2004 | Gray |
| 2004/0087213 A1 | 5/2004 | Kao |
| 2004/0099268 A1 | 5/2004 | Smith et al. |
| 2004/0101026 A1 | 5/2004 | Nitta et al. |
| 2004/0149284 A1 | 8/2004 | Smith et al. |
| 2004/0168530 A1 | 9/2004 | Adolfs |
| 2004/0182392 A1 | 9/2004 | Gerder et al. |
| 2004/0221843 A1 | 11/2004 | Baecke |
| 2004/0234254 A1 | 11/2004 | Czupich et al. |
| 2004/0239001 A1 | 12/2004 | Edirisuriya et al. |
| 2004/0244858 A1 | 12/2004 | Jeong |
| 2005/0039809 A1 | 2/2005 | Speldrich |
| 2005/0059957 A1 | 3/2005 | Campbell et al. |
| 2005/0152733 A1 | 7/2005 | Patel |
| 2006/0030191 A1 | 2/2006 | Tuin et al. |
| 2006/0118113 A1 | 6/2006 | Bremner et al. |
| 2006/0137445 A1 | 6/2006 | Smith et al. |
| 2006/0150712 A1 | 7/2006 | Berstis et al. |
| 2006/0165829 A1 | 7/2006 | Smith et al. |
| 2006/0196510 A1 | 9/2006 | McDonald et al. |
| 2006/0237012 A1 | 10/2006 | Thudor et al. |
| 2006/0249160 A1 | 11/2006 | Scarberry |
| 2006/0283450 A1 | 12/2006 | Shissler et al. |
| 2007/0039374 A1 | 2/2007 | Borali |
| 2007/0079982 A1 | 4/2007 | Laurent et al. |
| 2007/0107737 A1 | 5/2007 | Landis et al. |
| 2007/0110124 A1* | 5/2007 | Shiraki ............... G01K 1/14 374/208 |
| 2007/0144519 A1 | 6/2007 | Henry et al. |
| 2007/0157928 A1 | 7/2007 | Pujol et al. |
| 2007/0169776 A1 | 7/2007 | Kepler et al. |
| 2007/0175473 A1 | 8/2007 | Lewis et al. |
| 2007/0193580 A1 | 8/2007 | Feldhahn et al. |
| 2007/0248934 A1 | 10/2007 | Mosimann |
| 2007/0272240 A1 | 11/2007 | Aylsworth et al. |
| 2007/0284361 A1 | 12/2007 | Nadjafizadeh et al. |
| 2008/0000474 A1 | 1/2008 | Jochle et al. |
| 2008/0015257 A1 | 1/2008 | Grosskreutz et al. |
| 2008/0027344 A1 | 1/2008 | Terry |
| 2008/0051674 A1 | 2/2008 | Davenport et al. |
| 2008/0066741 A1 | 3/2008 | LeMahieu et al. |
| 2008/0066751 A1 | 3/2008 | Polacsek |
| 2008/0072900 A1 | 3/2008 | Kenyon et al. |
| 2008/0105257 A1 | 5/2008 | Klasek et al. |
| 2008/0142019 A1 | 6/2008 | Lewis et al. |
| 2008/0196716 A1 | 8/2008 | Wachter |
| 2008/0202512 A1 | 8/2008 | Kressierer/ Huber |
| 2008/0205481 A1 | 8/2008 | Faries |
| 2008/0205979 A1 | 8/2008 | Gombert et al. |
| 2008/0207028 A1 | 8/2008 | Schutz |
| 2008/0251073 A1 | 10/2008 | Jassell et al. |
| 2008/0264413 A1 | 10/2008 | Doherty et al. |
| 2008/0302362 A1 | 12/2008 | Kwok |
| 2008/0308169 A1 | 12/2008 | Nielsen et al. |
| 2009/0041080 A1 | 2/2009 | Koch |
| 2009/0044808 A1 | 2/2009 | Guney et al. |
| 2009/0050150 A1 | 2/2009 | Rossen et al. |
| 2009/0056712 A1 | 3/2009 | Cortez, Jr. et al. |
| 2009/0056713 A1 | 3/2009 | Cortez, Jr. et al. |
| 2009/0078259 A1 | 3/2009 | Kooji et al. |
| 2009/0107493 A1 | 4/2009 | Liu et al. |
| 2009/0107496 A1 | 4/2009 | McGhin et al. |
| 2009/0107501 A1 | 4/2009 | Krieger |
| 2009/0107981 A1 | 4/2009 | Andel et al. |
| 2009/0110022 A1 | 4/2009 | Snyder et al. |
| 2009/0110378 A1 | 4/2009 | Bradley et al. |
| 2009/0174092 A1 | 7/2009 | Kwok et al. |
| 2009/0180829 A1 | 7/2009 | Rejman et al. |
| 2009/0223514 A1 | 9/2009 | Smith et al. |
| 2009/0243226 A1 | 10/2009 | Liepold |
| 2009/0247989 A1 | 10/2009 | Burke |
| 2009/0301482 A1 | 12/2009 | Burton et al. |
| 2009/0320840 A1 | 12/2009 | Klasek et al. |
| 2010/0015830 A1 | 1/2010 | Simeon et al. |
| 2010/0083965 A1 | 4/2010 | Virr et al. |
| 2010/0087749 A1 | 4/2010 | Tovey |
| 2010/0102799 A1 | 4/2010 | Schnidrig |
| 2010/0116272 A1 | 5/2010 | Row et al. |
| 2010/0147301 A1 | 6/2010 | Kwok |
| 2010/0154796 A1 | 6/2010 | Smith et al. |
| 2010/0204602 A1 | 8/2010 | Addington et al. |
| 2010/0242963 A1 | 9/2010 | Brieger et al. |
| 2010/0272507 A1 | 10/2010 | Khoe |
| 2010/0292601 A1 | 11/2010 | Dompeling et al. |

(56) References Cited

U.S. PATENT DOCUMENTS

| | | |
|---|---|---|
| 2011/0017212 A1 | 1/2011 | Kenyon et al. |
| 2011/0023874 A1 | 2/2011 | Bath et al. |
| 2011/0046433 A1 | 2/2011 | Khodak |
| 2011/0046494 A1 | 2/2011 | Balji et al. |
| 2011/0073109 A1 | 3/2011 | Mayer et al. |
| 2011/0078109 A1 | 3/2011 | Mayer et al. |
| 2011/0088693 A1 | 4/2011 | Somervell et al. |
| 2011/0108031 A1 | 5/2011 | Korneff et al. |
| 2011/0114093 A1 | 5/2011 | Patil et al. |
| 2011/0155132 A1 | 6/2011 | Virr et al. |
| 2011/0180068 A1 | 7/2011 | Kenyon et al. |
| 2011/0186048 A1 | 8/2011 | Casse et al. |
| 2011/0247623 A1 | 10/2011 | McCarthy |
| 2011/0253136 A1 | 10/2011 | Sweeney et al. |
| 2011/0283999 A2 | 11/2011 | Smith et al. |
| 2011/0308518 A1 | 12/2011 | McGroary et al. |
| 2011/0313689 A1 | 12/2011 | Holley et al. |
| 2011/0316562 A1 | 12/2011 | Cefai et al. |
| 2012/0060838 A1 | 3/2012 | Lapoint et al. |
| 2012/0073573 A1 | 3/2012 | Thudor et al. |
| 2012/0125333 A1 | 5/2012 | Bedford et al. |
| 2012/0125334 A1 | 5/2012 | Korneff et al. |
| 2012/0146251 A1 | 6/2012 | Heine et al. |
| 2012/0174924 A1 | 7/2012 | Smith et al. |
| 2012/0215125 A1 | 8/2012 | Orr et al. |
| 2012/0227738 A1 | 9/2012 | Virr et al. |
| 2012/0255758 A1 | 10/2012 | Lee |
| 2012/0283570 A1 | 11/2012 | Tegg |
| 2012/0285448 A1 | 11/2012 | Dugan et al. |
| 2013/0008158 A1 | 1/2013 | Hon |
| 2013/0042867 A1 | 2/2013 | Kwok et al. |
| 2013/0043677 A1 | 2/2013 | Gibson |
| 2013/0079667 A1 | 3/2013 | Berkcan et al. |
| 2013/0081619 A1 | 4/2013 | Seakins et al. |
| 2013/0087143 A1 | 4/2013 | Pujol |
| 2013/0104888 A1 | 5/2013 | Landis et al. |
| 2013/0104901 A1 | 5/2013 | Landis et al. |
| 2013/0112201 A1 | 5/2013 | Graham et al. |
| 2013/0112202 A1 | 5/2013 | Fogelbrink |
| 2013/0152931 A1 | 6/2013 | Sims et al. |
| 2013/0174839 A1 | 7/2013 | Ging et al. |
| 2013/0199529 A1 | 8/2013 | Power et al. |
| 2013/0206140 A1 | 8/2013 | Kepler et al. |
| 2013/0237781 A1 | 9/2013 | Gyrn |
| 2013/0239960 A1 | 9/2013 | Bertinetti et al. |
| 2013/0239966 A1 | 9/2013 | Klasek et al. |
| 2013/0247905 A1 | 9/2013 | Miller et al. |
| 2013/0248044 A1 | 9/2013 | Shiga et al. |
| 2013/0252461 A1 | 9/2013 | Gross |
| 2013/0255677 A1 | 10/2013 | Varga |
| 2013/0333701 A1 | 12/2013 | Herron |
| 2013/0340752 A1 | 12/2013 | Landis et al. |
| 2014/0007872 A1 | 1/2014 | Grundler et al. |
| 2014/0020684 A1 | 1/2014 | Klasek et al. |
| 2014/0048065 A1 | 2/2014 | Haroutunian |
| 2014/0090649 A1 | 4/2014 | Groll et al. |
| 2014/0116433 A1 | 5/2014 | Ghalib et al. |
| 2014/0130802 A1 | 5/2014 | Virr et al. |
| 2014/0202460 A1 | 7/2014 | Bath et al. |
| 2014/0202463 A1 | 7/2014 | Ging et al. |
| 2014/0216446 A1 | 8/2014 | Wruck |
| 2014/0251322 A1 | 9/2014 | Miller |
| 2014/0251331 A1 | 9/2014 | Korneff et al. |
| 2014/0283829 A1 | 9/2014 | Miller |
| 2014/0311489 A1 | 10/2014 | Heine et al. |
| 2014/0318536 A1 | 10/2014 | Landis et al. |
| 2014/0331786 A1 | 11/2014 | Romano |
| 2014/0338666 A1 | 11/2014 | Visveshwara et al. |
| 2014/0345614 A1 | 11/2014 | Kwok |
| 2014/0366876 A1 | 12/2014 | Huby et al. |
| 2015/0027204 A1* | 1/2015 | Stoks .................. A61M 16/161 73/31.05 |
| 2015/0040897 A1 | 2/2015 | Buechi |
| 2015/0048530 A1 | 2/2015 | Cheung et al. |
| 2015/0083126 A1 | 3/2015 | Rogers |
| 2015/0083132 A1 | 3/2015 | Jones et al. |
| 2015/0090260 A1 | 4/2015 | Seakins et al. |
| 2015/0096560 A1 | 4/2015 | Klenner et al. |
| 2015/0107588 A1 | 4/2015 | Cheung et al. |
| 2015/0144130 A1 | 5/2015 | O'Donnell et al. |
| 2015/0186725 A1 | 7/2015 | Oates et al. |
| 2015/0359990 A1 | 12/2015 | Barker et al. |
| 2016/0008560 A1 | 1/2016 | Kwok |
| 2016/0015927 A1 | 1/2016 | Winski et al. |
| 2016/0015937 A1 | 1/2016 | Winski et al. |
| 2016/0022954 A1 | 1/2016 | Bath et al. |
| 2016/0051789 A1 | 2/2016 | Korneff et al. |
| 2016/0089510 A1 | 3/2016 | Korneff et al. |
| 2016/0101258 A1 | 4/2016 | Rustad et al. |
| 2016/0189612 A1 | 7/2016 | Foote et al. |
| 2016/0199612 A1 | 7/2016 | Foote et al. |
| 2016/0256642 A1 | 9/2016 | Soysa et al. |
| 2016/0256657 A1 | 9/2016 | Klasek et al. |
| 2016/0296721 A1 | 10/2016 | Landis et al. |
| 2016/0310691 A1 | 10/2016 | Bath et al. |
| 2016/0367776 A1 | 12/2016 | Landis et al. |
| 2016/0367779 A1 | 12/2016 | Landis et al. |
| 2017/0000968 A1 | 1/2017 | Harrington et al. |
| 2017/0085635 A1 | 4/2017 | Huby |
| 2017/0136188 A1 | 5/2017 | Delangre et al. |
| 2017/0151411 A1* | 6/2017 | Osborne .................. G01K 1/08 |
| 2017/0161461 A1 | 6/2017 | Delangre et al. |
| 2017/0173293 A1 | 6/2017 | Osborne et al. |
| 2017/0197057 A1 | 7/2017 | Osborne et al. |
| 2017/0239432 A1 | 8/2017 | Delangre et al. |
| 2017/0326320 A1 | 11/2017 | Baigent et al. |
| 2018/0078730 A1 | 3/2018 | Bath et al. |
| 2018/0169361 A1 | 6/2018 | Dennis et al. |
| 2018/0250491 A1 | 9/2018 | Row et al. |
| 2018/0296791 A1 | 10/2018 | Klenner et al. |
| 2019/0197057 A1 | 6/2019 | Yan et al. |
| 2019/0255278 A1 | 8/2019 | Osborne et al. |
| 2020/0101253 A1 | 4/2020 | Osborne et al. |
| 2021/0220601 A1 | 7/2021 | Stoks et al. |

FOREIGN PATENT DOCUMENTS

| | | |
|---|---|---|
| AU | 2000071791 | 3/2001 |
| AU | 2001028104 | 9/2001 |
| AU | 2002244571 | 9/2002 |
| AU | 2007317198 | 5/2008 |
| AU | 2010206053 | 2/2011 |
| AU | 2013201490 | 4/2013 |
| CA | 1202862 | 4/1986 |
| CA | 2464530 | 5/2003 |
| CA | 2495451 | 3/2004 |
| CA | 2535974 | 10/2011 |
| CA | 2393743 | 1/2012 |
| CA | 2852215 | 4/2013 |
| CN | 2243015 Y | 12/1996 |
| CN | 1598510 | 3/2005 |
| CN | 1688358 | 10/2005 |
| CN | 101666664 | 3/2010 |
| CN | 102844645 A | 12/2012 |
| CN | 201672170 | 12/2015 |
| DE | 3110903 | 9/1982 |
| DE | 3618614 | 12/1987 |
| DE | 4020522 | 1/1992 |
| DE | 4102223 | 7/1992 |
| DE | 19647548 | 5/1998 |
| DE | 19958296 | 9/2001 |
| DE | 20 2004 006 484 | 9/2005 |
| DE | 102004030747 | 1/2006 |
| DE | 20 2005 008 152 | 10/2006 |
| DE | 20 2005 008 156 | 10/2006 |
| DE | 203 21 468 | 8/2007 |
| DE | 203 21 469 | 8/2007 |
| DE | 203 21 470 | 8/2007 |
| DE | 203 21 471 | 8/2007 |
| DE | 203 21 472 | 8/2007 |
| DE | 20 2006 007 397 | 9/2007 |
| DE | 20 2004 021 759 | 10/2007 |
| DE | 20 2006 011 754 | 12/2007 |
| DE | 201 22 844 | 5/2008 |

(56) References Cited

FOREIGN PATENT DOCUMENTS

| | | |
|---|---|---|
| DE | 102007003454 | 7/2008 |
| DE | 102007003455 | 8/2008 |
| DE | 102007039391 | 2/2009 |
| DE | 102008001022 | 10/2009 |
| DE | 20 2004 021 757 | 9/2010 |
| DE | 20 2004 021 758 | 9/2010 |
| DE | 201 22 937 | 9/2010 |
| DE | 20 2004 021 756 | 10/2010 |
| DE | 20 2004 021 774 | 11/2010 |
| DE | 20 2004 021 777 | 12/2010 |
| DE | 20 2004 021 794 | 2/2011 |
| DE | 20 2004 021 795 | 2/2011 |
| DE | 20 2004 021 796 | 2/2011 |
| DE | 20 2004 021 798 | 2/2011 |
| DE | 20 2006 020 951 | 2/2011 |
| DE | 20 2006 020 952 | 2/2011 |
| DE | 20 2004 021829 | 5/2011 |
| DE | 201 22 943 | 5/2011 |
| DE | 201 22 944 | 5/2011 |
| DE | 201 22 945 | 5/2011 |
| DE | 20 2005 021 927 | 6/2011 |
| DE | 20 2006 021 019 | 11/2011 |
| DE | 203 21 882 | 12/2011 |
| DE | 20 2004 021876 | 1/2012 |
| DE | 20 2007 019350 | 1/2012 |
| DE | 20 2011 107 902 | 1/2012 |
| DE | 20 2010 016 037 | 3/2012 |
| DE | 20 2012 007 229 | 10/2012 |
| DE | 102007039391 | 6/2016 |
| EP | 0 111 248 | 6/1984 |
| EP | 0050984 | 12/1984 |
| EP | 0201985 | 11/1986 |
| EP | 0291921 | 11/1988 |
| EP | 0535952 | 4/1993 |
| EP | 0567158 | 10/1993 |
| EP | 0 232 864 | 5/1994 |
| EP | 0885623 | 12/1998 |
| EP | 1262208 | 12/2002 |
| EP | 1352670 | 10/2003 |
| EP | 1 396 277 | 3/2004 |
| EP | 0885623 | 11/2004 |
| EP | 1 535 722 | 6/2005 |
| EP | 1646910 | 4/2006 |
| EP | 1129743 | 5/2006 |
| EP | 1669098 | 6/2006 |
| EP | 1035887 | 7/2006 |
| EP | 1683066 | 7/2006 |
| EP | 1457223 B1 | 10/2006 |
| EP | 1741462 | 1/2007 |
| EP | 1837640 A2 | 9/2007 |
| EP | 1055431 | 11/2007 |
| EP | 1924311 | 5/2008 |
| EP | 1933914 | 6/2008 |
| EP | 1979030 | 10/2008 |
| EP | 2079505 | 7/2009 |
| EP | 2089086 | 8/2009 |
| EP | 2101851 | 9/2009 |
| EP | 2195061 | 6/2010 |
| EP | 2236167 | 10/2010 |
| EP | 2282795 | 2/2011 |
| EP | 2307082 | 4/2011 |
| EP | 2335761 | 6/2011 |
| EP | 2340867 | 7/2011 |
| EP | 2355881 | 8/2011 |
| EP | 2 133 611 | 9/2011 |
| EP | 2415445 | 2/2012 |
| EP | 2471568 | 7/2012 |
| EP | 2498854 | 9/2012 |
| EP | 2281138 | 10/2012 |
| EP | 2514478 | 10/2012 |
| EP | 2575944 | 4/2013 |
| EP | 2629080 | 8/2013 |
| EP | 2640451 | 9/2013 |
| EP | 2651481 | 10/2013 |
| EP | 2654869 | 10/2013 |
| EP | 2667919 | 12/2013 |
| EP | 2522255 | 3/2014 |
| EP | 2703034 A2 | 3/2014 |
| EP | 2760516 | 8/2014 |
| EP | 2830695 | 2/2015 |
| EP | 2877224 | 6/2015 |
| EP | 3013402 | 5/2016 |
| EP | 1359962 | 8/2016 |
| EP | 3053623 | 8/2016 |
| EP | 3148418 | 4/2017 |
| EP | 2640451 | 6/2017 |
| EP | 3082920 | 10/2017 |
| EP | 3148419 | 1/2018 |
| GB | 1310949 | 3/1973 |
| GB | 1364127 | 8/1974 |
| GB | 2176313 | 12/1986 |
| GB | 2224957 | 5/1990 |
| GB | 2504284 A | 1/2014 |
| JP | 59-113392 | 6/1984 |
| JP | H0623051 | 2/1994 |
| JP | 11-033119 | 2/1999 |
| JP | 11-286058 | 10/1999 |
| JP | 2001095920 | 4/2001 |
| JP | 2001-129091 A | 5/2001 |
| JP | 2001-511507 | 8/2001 |
| JP | 2003-139276 | 5/2003 |
| JP | 03194747 | 7/2003 |
| JP | 2003275312 | 9/2003 |
| JP | 2008132370 | 6/2008 |
| JP | 4242816 | 3/2009 |
| JP | 44-022293 | 2/2010 |
| JP | 2011125618 | 6/2011 |
| JP | 11248076 | 12/2011 |
| JP | H 05208935 | 6/2013 |
| NZ | 564886 | 2/2011 |
| NZ | 587113 | 12/2011 |
| NZ | 586325 | 1/2012 |
| NZ | 597020 | 6/2013 |
| NZ | 604137 | 6/2014 |
| NZ | 610299 | 11/2014 |
| NZ | 630762 | 2/2016 |
| NZ | 625605 | 4/2016 |
| NZ | 710078 | 1/2017 |
| NZ | 710351 | 1/2017 |
| NZ | 631008 | 7/2017 |
| NZ | 733931 | 2/2019 |
| TW | 201245604 | 11/2012 |
| WO | WO 1996/020748 | 7/1996 |
| WO | WO 97/18001 | 5/1997 |
| WO | WO 1997/042475 A1 | 11/1997 |
| WO | WO 2000/029057 | 5/2000 |
| WO | WO 2001/032069 | 5/2001 |
| WO | WO 01/41854 | 6/2001 |
| WO | WO 01/97894 | 12/2001 |
| WO | WO 2002/017991 | 3/2002 |
| WO | WO 02/066106 | 8/2002 |
| WO | WO 02/066107 | 8/2002 |
| WO | WO 2002/066106 | 8/2002 |
| WO | WO 2002/075854 | 9/2002 |
| WO | WO 2003/026721 | 4/2003 |
| WO | WO 2004/011072 | 2/2004 |
| WO | WO 2004/024429 | 3/2004 |
| WO | WO 2004/037330 | 5/2004 |
| WO | WO 2004/092955 | 11/2004 |
| WO | WO 2004/093954 | 11/2004 |
| WO | WO 2004/093955 | 11/2004 |
| WO | WO 2005/011785 | 2/2005 |
| WO | WO 2005/021076 | 3/2005 |
| WO | WO 2005/079670 A1 | 9/2005 |
| WO | WO 2006/017350 | 2/2006 |
| WO | WO 2006/019323 | 2/2006 |
| WO | WO 2007/019626 | 2/2007 |
| WO | WO 2007/043060 | 4/2007 |
| WO | WO 2007/051230 | 5/2007 |
| WO | WO 2008/055308 | 5/2008 |
| WO | WO 2008/056993 | 5/2008 |
| WO | WO 2008/058328 | 5/2008 |
| WO | WO 2008/060046 | 5/2008 |
| WO | WO 2008/060295 | 5/2008 |

(56) References Cited

FOREIGN PATENT DOCUMENTS

| WO | WO 2008/076230 | 6/2008 | |
|---|---|---|---|
| WO | WO 2008/097211 | 12/2008 | |
| WO | WO 2009/002004 | 12/2008 | |
| WO | WO 2009/006586 | 1/2009 | |
| WO | WO 2009/022004 | 2/2009 | |
| WO | WO 2009/127192 A1 | 10/2009 | |
| WO | WO 2009/146484 | 12/2009 | |
| WO | WO 2010/031125 | 3/2010 | |
| WO | WO 2010/031126 | 3/2010 | |
| WO | WO 2010/091259 | 8/2010 | |
| WO | WO 2011/030251 A1 | 3/2011 | |
| WO | WO 2011/059622 | 5/2011 | |
| WO | WO 2012/053910 | 4/2012 | |
| WO | WO 2012/065999 | 5/2012 | |
| WO | WO 2012/065999 A2 | 5/2012 | |
| WO | WO 2012/087644 | 6/2012 | |
| WO | WO 2012/100291 | 8/2012 | |
| WO | WO 2012/154883 | 11/2012 | |
| WO | WO 2012/164407 | 12/2012 | |
| WO | WO 2013/022356 A1 | 2/2013 | |
| WO | WO 2013/026901 | 2/2013 | |
| WO | WO 2013/045572 | 4/2013 | |
| WO | WO 2013/045575 | 4/2013 | |
| WO | WO 2013/045575 A1 | 4/2013 | |
| WO | WO 2013/045586 | 4/2013 | |
| WO | WO 2013/049660 | 4/2013 | |
| WO | WO 2013/050907 | 4/2013 | |
| WO | WO 2013/050907 A1 | 4/2013 | |
| WO | WO 2013/088351 | 6/2013 | |
| WO | WO 2013/127474 | 9/2013 | |
| WO | WO 2013/137753 | 9/2013 | |
| WO | WO 2013/137753 A1 | 9/2013 | |
| WO | WO 2013/151447 | 10/2013 | |
| WO | WO 2013/162386 | 10/2013 | |
| WO | WO 2014/015382 | 1/2014 | |
| WO | WO 2014/055407 | 4/2014 | |
| WO | WO 2014/077706 | 5/2014 | |
| WO | WO 2014/138804 | 9/2014 | |
| WO | WO 2014/205513 | 12/2014 | |
| WO | WO 2015/038013 A1 | 3/2015 | |
| WO | WO-2015038013 A1 * | 3/2015 | ............... G01K 1/08 |
| WO | WO 2015/060729 | 4/2015 | |
| WO | WO 2015/119515 A1 | 8/2015 | |
| WO | WO 2015/160268 | 10/2015 | |
| WO | WO 2015/179916 | 12/2015 | |
| WO | WO 2016/042522 | 3/2016 | |
| WO | WO 2016/089224 | 6/2016 | |
| WO | WO 2016/139645 | 6/2016 | |
| WO | WO 2017/027906 | 2/2017 | |
| WO | WO 2017/126980 | 7/2017 | |

OTHER PUBLICATIONS

International Search Report; PCT/NZ2015/050011; dated Mar. 19, 2015; 3 pages.
Jul. 9, 2013 International Search Report and Written Opinion for International Application No. PCT/NZ2013/000042 filed on Mar. 15, 2013.
International Preliminary Report on Patentability; Application No. PCT/IB2012/001786; Filed May 30, 2012.
International Search Report; PCT/IB2012/001786; dated Nov. 21, 2012.
International Preliminary Report on Patentability dated Jun. 9, 2015 for PCT Application No. PCT/NZ2013/000222 filed on Dec. 4, 2013.
The Pacific Energy Association Reporter, Summer Issue, 1992, vol. II, pp. 13-17.
Extended European Search Report for Application No. 15803457.9 dated Nov. 28, 2017, 8 pages.
Chinese Examination Report for Application No. 201580038988.3 dated Aug. 30, 2018.
Sep. 4, 2015, International Search Report for PCT/NZ2015/050069 filed on Jun. 3, 2015.
International Search Report for International App. No. PCT/NZ2017/050157, dated May 9, 2018, in 10 pages.
Sawyer, Dick, et al. "An introduction to human factors in medical devices." US Department of Health and Human Services, Public Health Service, Food and Drug Administration, Center for Devices and Radiological Health (1996).

* cited by examiner

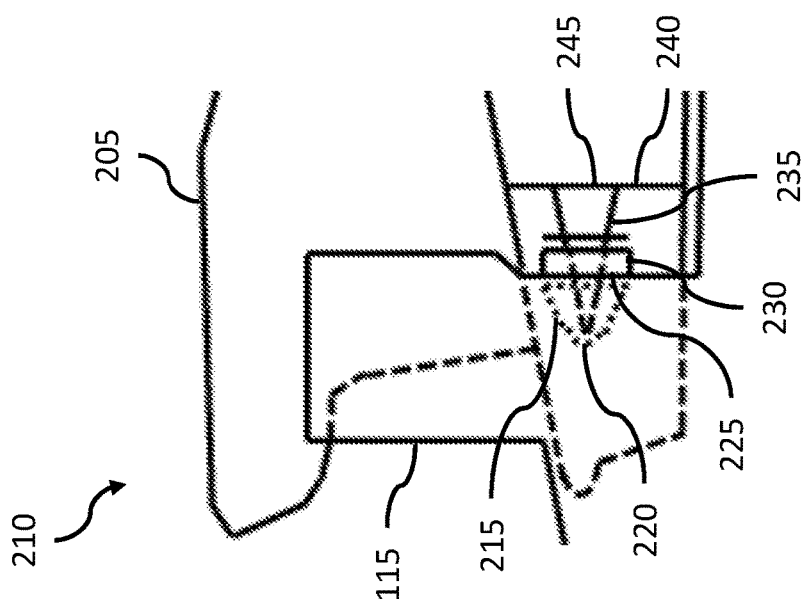
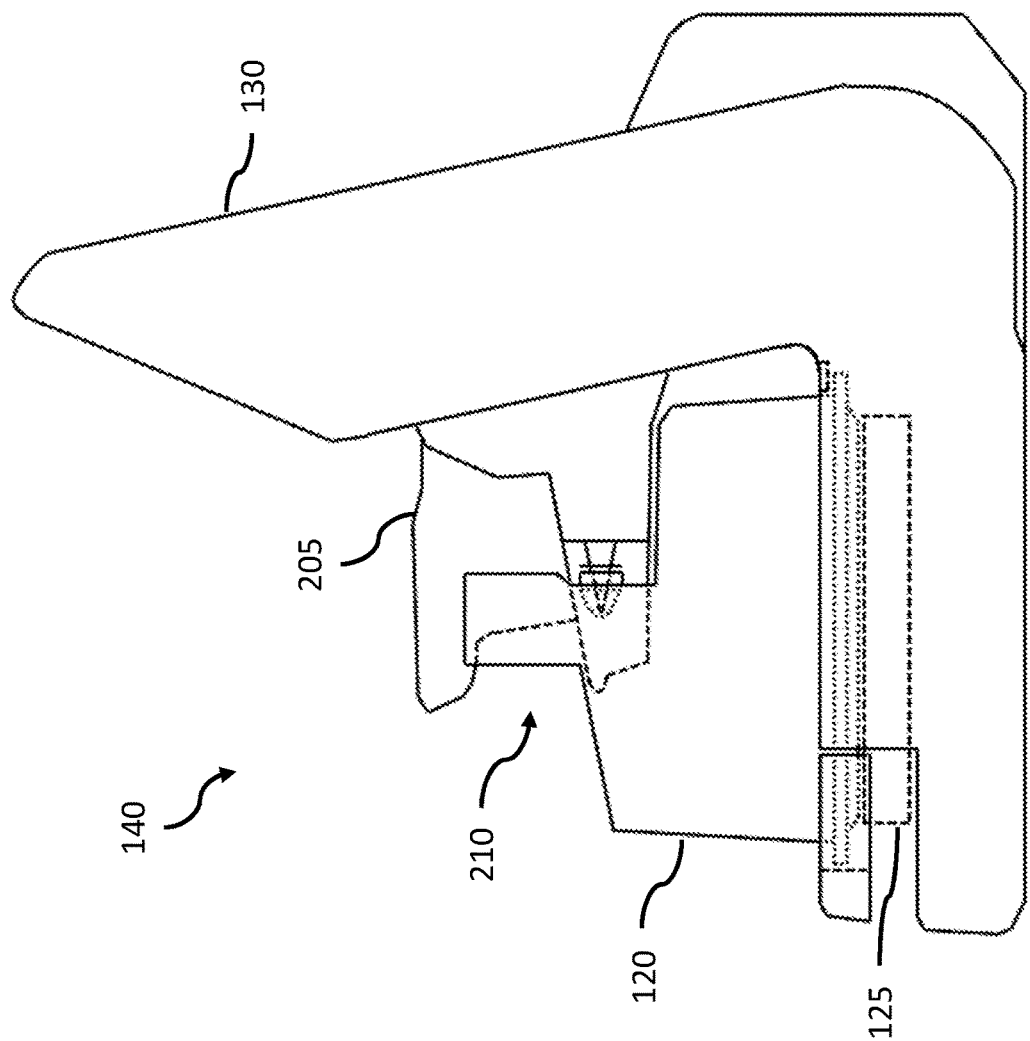
Fig. 2B
Fig. 2A

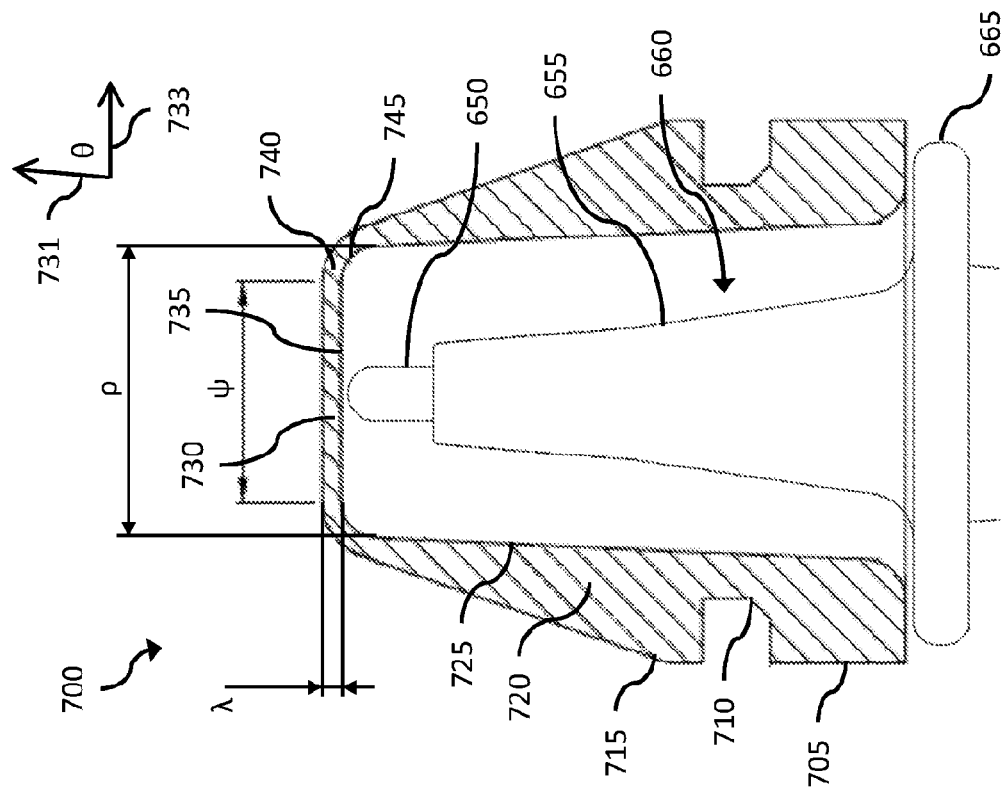
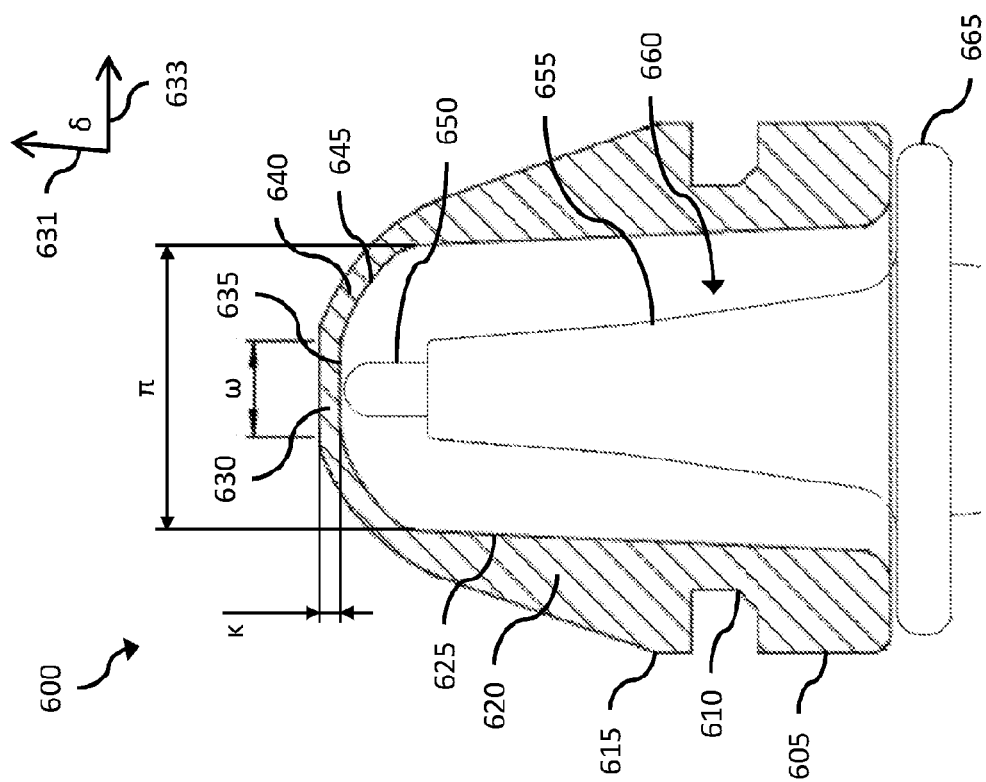

SENSING ARRANGEMENTS FOR MEDICAL DEVICES

PRIORITY

This utility application claims priority to U.S. Provisional Patent Application No. 62/431,372, entitled "Sensing Arrangements for Medical Devices," and filed Dec. 7, 2016, the entire contents of which are hereby incorporated by this reference.

BACKGROUND

Technical Field

The present disclosure generally relates to devices and methods for providing heated and/or humidified gases to a user. More particularly, certain features, aspects and advantages of the present disclosure relate to a sensing arrangement for a medical device such as a respiratory humidification system, a positive airway pressure system, a high flow system, an insufflation system and/or a ventilator.

Description of the Related Art

A sensing arrangement for a medical device may include a feature to provide, in whole or in part, for positioning of the sensing arrangement; for example, the sensing arrangement may include a more flexible component to allow alignment tolerance between a sensing element of the sensing arrangement and a desired measurement position or orientation. A sensing arrangement for a medical device may include a feature to provide, in whole or in part, for protection of the sensing arrangement; for example, the sensing arrangement may include a more rigid component to protect the sensing arrangement from damage caused by forces exerted against the sensing arrangement during use.

However, a sensing arrangement for a medical device may include multiple positioning and/or protection features that may conflict with each other; for example, a more flexible component that improves positioning of the sensing arrangement may reduce protection of the sensing arrangement, and a more rigid component that improves protection of the sensing arrangement may detract from positioning of the sensing arrangement. There is a need for a sensing arrangement for a medical device that includes features to collectively provide for positioning and protection of the sensing arrangement.

BRIEF SUMMARY

A sensing arrangement for a medical device is disclosed that includes features to collectively provide for positioning and protection of the sensing arrangement.

According to at least one aspect of the present disclosure, a sensing arrangement for a medical device includes one, some, or all of the following features, as well as other features described herein. The sensing arrangement includes a housing. The housing includes a rigid portion and a flexible portion. The rigid portion includes a tip and a stem. An exterior of the rigid portion extends from the tip to the stem. The flexible portion includes a collar region and a tail region. An exterior of the flexible portion extends from the collar region to the tail region. A rear flange protrudes from the exterior of the flexible portion in the tail region. A front flange protrudes from the exterior of the flexible portion between the collar region and the rear flange. A throat region of the exterior of the flexible portion is between the front flange and the rear flange. An interior of the flexible portion extends from the collar region to the tail region. The collar region is attached to the exterior of the rigid portion between the tip and the stem. The stem may be positioned within the interior of the flexible portion between a first plane passing through the collar region and a second plane passing through the throat region. The stem may alternatively be positioned within the flexible portion between a first plane passing through the tail region and a second plane passing through the throat region.

The sensing arrangement can include an interior passageway of the rigid portion. The interior passageway can extend from the tip to the stem. A sensing element can be positioned at least partially within the interior passageway at the tip.

The sensing arrangement can include at least one wire. The at least one wire can be attached to the sensing element. The at least one wire can extend through the interior passageway to the stem and into the interior of the flexible portion.

The collar region may be configured to roll over a portion of the rigid portion as the rigid portion moves axially. The collar region may comprise a curved region that is configured to roll over an attachment region, the attachment region being the region where the flexible portion connects to the rigid portion. Preferably, through forming of the collar region from a resilient material, or some other manner such as an external biasing means, on insertion of the sensing arrangement through an aperture, in, for example, a chamber, the collar region remains partially compressed. This can aid in establishing the correct orientation of the sensing arrangement and improve sealing about said aperture by increasing the force between a seal and the wall defining the aperture. Further, this spring force can assist in disengaging the sensing arrangement from the wall about the aperture through its tendency to push against said wall, performing an "auto-eject" function. Thus, for example, a chamber may be locked in position against a heater base with the collar region partially compressed. When the lock is released, the chamber is then biased away from the sensing arrangement and the base, facilitating removal. Of course, this assumes that the sensing arrangements extend in a direction that opposes the direction in which the chamber is slid into engagement with the heater base although other arrangements are possible including slidable mountings for the sensing arrangement(s).

The collar region is preferably thicker than the throat region.

The rear flange may have a height that is three quarters or more than a height of a baffle, wherein the baffle is arranged on a wall of a heater base or a wall of a removable component that is adapted to couple to the heater base.

The wall of the heater base or the removable component may include a pair of baffles that are spaced apart from each other, the rear flange being received between the baffles to prevent rotation of the rear flange.

The sensing arrangement may include one or more seals, the seals engaging the housing in use to protect the housing and a sensor associated with the housing. The one or more seals may have a target region that contacts the sensor in an operative position. The target region may be substantially planar. A width of the target region may be 90% or more of the width of an opening in the seal, wherein the opening is configured to receive the housing and sensor within it.

The seal may comprise a cap portion, said target portion forming at least part of the cap portion, the cap portion comprising at least a portion configured to stretch when the housing and sensor within it is received therein.

The housing may comprise a sealing flange provided between the tip and the collar region, the sealing flange for sealingly mating with the seal at an end thereof distal from the target region. The sealing flange may protrude from the exterior of the rigid portion.

The seal may define an internal passageway that is closed at a first end, said first end being formed at least in part by the target region, wherein, at rest (with the seal not being stretched by the housing), a length of said passageway is less than a length of the housing between the tip and the sealing flange. According to this embodiment, the seal is preferably configured to stretch such that a second end of the seal contacts the sealing flange when in an operative position with the housing received inside the passageway, the second end being distal from the first end and defining an opening into the passageway. Alternatively, the passageway may be substantially the same length as the portion of the housing received therein when in an operative position for sensing. According to such embodiments, the seal may or may not be configured to stretch. The stretching of the seal can additionally or alternatively perform an "auto-eject" function by urging the sensing arrangement away from, for example, a chamber.

At least part of the flexible portion may be resiliently deformable and/or act as a spring or resilient member such that the rigid portion is urged towards a rest position.

According to another aspect, a sensing arrangement for a medical device includes a housing for supporting a sensor, the housing including a flexible portion that is resiliently deformable and/or acts as a spring or resilient member. Other, preferred features of this aspect may be taken from the other aspects and the description of the preferred embodiments.

According to another aspect, there is provided a removable component for a medical device comprising a sensing arrangement according to any of the preceding aspects. The removable component may comprise a wall having an aperture therein, the aperture being configured to receive at least a portion of the housing of the sensing arrangement therein. The aperture is preferably dimensioned to receive the housing such that the wall is positioned between the rear flange and the front flange.

The removable component may be configured to permanently or removably couple to said medical device. The coupling may comprise a structural coupling, fixing the removable component in position relative to the medical device. The coupling may additionally or alternatively comprise an electrical and/or communicative coupling for enabling signals from sensor(s) of the sensing arrangement, or data derived therefrom, to be communicated to the medical device and/or for components of the sensing arrangement to be electrically powered and/or for other communications to be exchanged with the removable component such as configuration data.

According to another aspect, there is provided a medical device comprising a sensing arrangement and/or a removable component according to any one or more of the previous aspects.

The medical device may comprise a heater base, the heater base being configured to receive a liquid chamber and heat the contents thereof. Upon engagement of the chamber with the heater base, at least a portion of the housing of the sensing arrangement may be received in an aperture in the chamber, said aperture preferably being provided in an inlet port or an outlet port of the chamber.

The medical device may comprise, or be adapted to fluidly couple to, a gases source. The gases source may, for example, comprise a blower or ventilator.

According to another aspect, there is provided a seal for use with apparatus of any one or more of the prior aspects. The seal preferably comprises a base portion joined to a cap portion by an inset region, the seal defining a passageway, the passageway being open at a first end at the base portion for receiving at least a portion of a housing of a sensing arrangement therein.

Preferably, the seal is closed at a second end at the cap portion. The inset region may be configured to be received inside an aperture in a wall with the cap portion on a first side of the wall and the base portion on the other, second side of said wall, said sensing arrangement being adapted to sense a parameter of a gas on the first side of the wall.

The seal may comprise a target region that contacts a sensor of the sensing arrangement. The target region may be substantially planar. The width of the target region may be 50%, preferably 70% and more preferably 90% or more of the width of an opening in the seal, wherein the opening is configured to receive the housing and sensor within it.

The target portion may form at least part of the cap portion. The cap portion may comprise at least a portion configured to stretch when the housing and sensor within it is received therein.

The housing may comprise a sealing flange provided between the tip and the collar region, with the base portion being configured to sealingly mating with the sealing flange.

According to another aspect, there is provided a humidification chamber adapted for use with the apparatus of any one or more of the prior aspects. More particularly, said chamber may comprise one or more apertures, preferably in ports thereof, for receiving one or more sensing arrangements therethrough, or at least sensing portions or probes thereof.

According to another aspect there is provided a system comprising apparatus according to any one or more of the prior aspects. The system may also comprise any one or more of a supply tube, a delivery tube, an expiratory tube, a patient interface, a liquid chamber.

According to embodiments of the above aspects, a sensing arrangement, or at least a sensing portion thereof, may be adapted so as to be inserted into an aperture in an inlet port or an outlet port of a chamber, particularly a humidification chamber. However, apertures may be positioned elsewhere, depending on where it is desired to perform the sensing. Further, more than one aperture may be provided adjacent one another, such as in the inlet port and/or the outlet port, each being positioned and configured to receive at least one sensing arrangement therethrough. A said aperture may be configured to receive more than one sensing arrangement therethrough and/or more than one sensing portion of the same sensing arrangement. As will be appreciated, particularly where sensing arrangements or portions or probes thereof are provided in close proximity, such as at the same port of a chamber, it may be desirable to provide common components of or integration between the sensing arrangements. Thus, rather than there necessarily being a separate sensing arrangement provided for each sensor supported by the sensing arrangement, the same sensing arrangement may have more than one sensing portion or probe extending therefrom, each supporting a sensor. Further, each sensing arrangement (or portion or probe) may include more than one sensor.

Additionally or alternatively, sensing arrangements may interface with the gases elsewhere along their path, such as via aperture(s) provided in other positions on the chamber (e.g. the main sidewall or the top), along one of the tubes used to convey gases between the gases source and the patient interface, the patient interface or cuff connectors used to sealingly connect components of the system together. Further, it will be appreciated that the sensing arrangement could also be used to sense parameters of a liquid, such as the liquid in a humidification chamber, were it considered desirable to do so.

According to some embodiments applied to a humidification chamber, one or two apertures may be provided in an inlet port each for receiving a respective one or more sensing arrangements or at least a sensing portion or probe thereof. Additionally, or alternatively, one or two apertures may be provided in an outlet port of a chamber, each for receiving a respective one or more sensing arrangements or sensing portion or probe thereof. According to a presently preferred embodiment, temperature is measured at an inlet port and an outlet port of a chamber and flow is measured at one or both of the ports, preferably the outlet port. Respective seals as described herein may be provided for each said aperture. Where adjacent apertures are provided, a single seal may be provided to seal both apertures. For example, base portions of the seal may be linked via a web. Additionally, or alternatively, a single seal may be configured to receive more than one sensing arrangement (or at least sensing portion or probe thereof) and sealing mate with a single aperture, such as in a port of a chamber. Again, this may, for example, be effected using a web joining base portions of the seals.

BRIEF DESCRIPTION OF THE DRAWINGS

FIG. 2A illustrates an example embodiment of the medical device of FIG. 1.

FIG. 2B illustrates an enlargement of a portion of the medical device of FIG. 2A including an example embodiment of a sensing arrangement.

FIG. 6 illustrates a side cross-sectional view of an example embodiment of the seal of FIG. 2B and a portion of an example embodiment of the sensing arrangement of FIG. 2B.

FIG. 7 illustrates a side cross-sectional view of an example embodiment of the seal of FIG. 2B and a portion of an example embodiment of the sensing arrangement of FIG. 2B.

DETAILED DESCRIPTION

Certain embodiments and examples of housings for medical devices are described herein. Those of skill in the art will appreciate that the disclosure extends beyond the specifically disclosed embodiments and/or uses and obvious modifications and equivalents thereof. Thus, it is intended that the scope of the disclosure should not be limited by any particular embodiments described herein.

Figure 1:
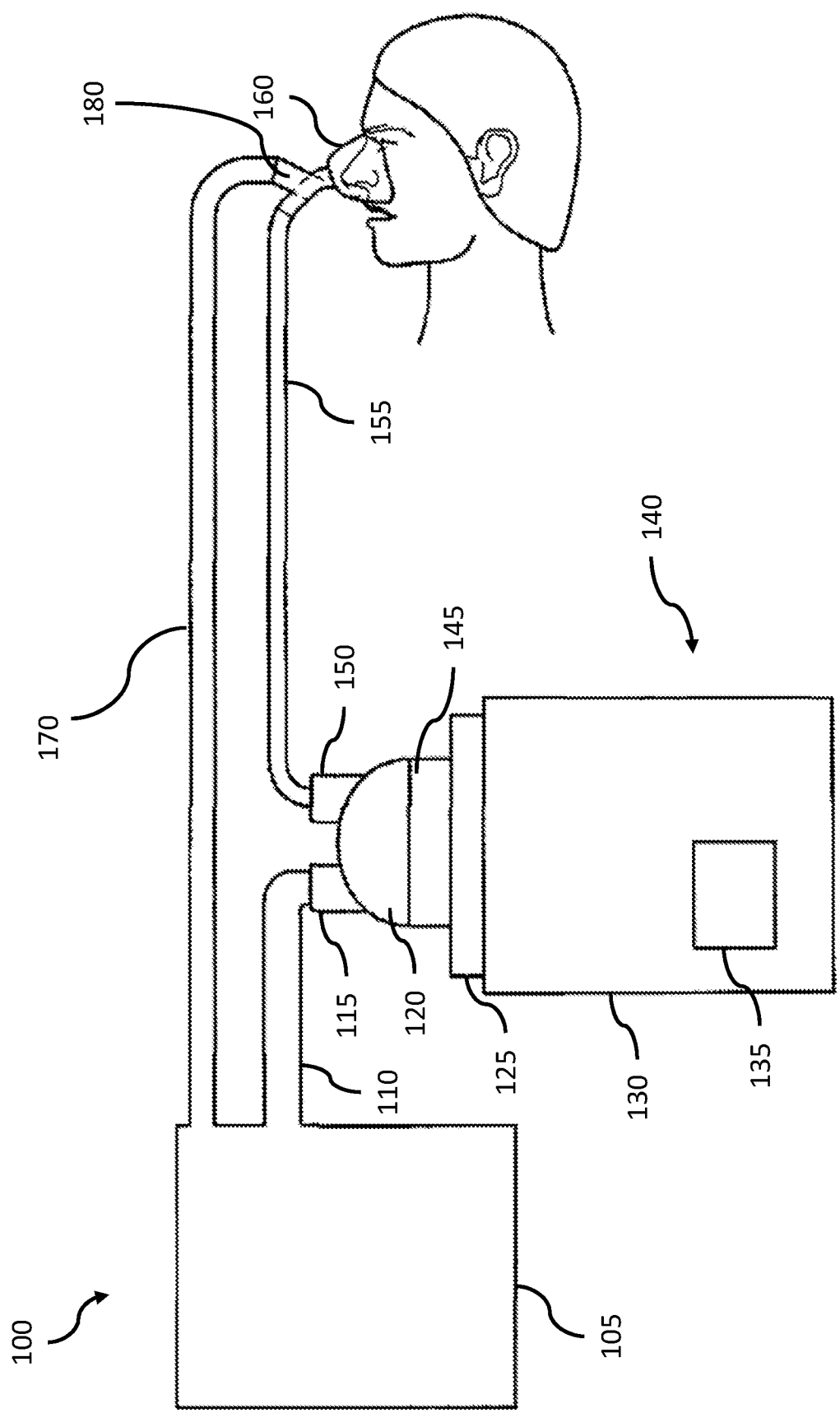
FIG. 1 illustrates an example embodiment of a medical system that includes a medical device.

FIG. 1 schematically illustrates an example embodiment of a medical system 100 that can be used to deliver gases to a patient or other user. The medical system 100 can be used, in some applications, to provide respiratory therapy, including but not limited to invasive ventilation, non-invasive ventilation, positive pressure therapy, or high flow therapy, or to provide gases for surgical procedures, including but not limited to laparoscopic or open site surgical procedures.

An example embodiment of the medical system 100 can include a medical device 140 adapted to condition gases, for example to heat and/or humidify gases, to be delivered to a patient or other user. The medical device 140 can include a base 130 and a chamber 120. The base 130 can include a heater 125. The chamber 120 can include an inlet port 115 and an outlet port 150. A supply tube 110 can provide fluid communication from a gases source 105 to the inlet port 115. A delivery tube 155 can provide fluid communication from the outlet port 150 to a patient interface 160. The system 100 of FIG. 1 is shown as also including an expiratory tube 170 connecting between the patient interface 160, via wye piece 180, and the gases source 105. According to some embodiments the expiratory tube may be omitted with surplus and exhaled gases being vented to ambient air and/or directed elsewhere. More generally, the invention is not limited to any particular arrangement of the pneumatic circuit.

In an embodiment, the chamber 120 is adapted to be removably mounted on the base 130 adjacent to the heater 125. Gases supplied by the gases source 105 flow through the supply tube 110 into the chamber 120 via the inlet port 115 and from the chamber 120 via the outlet port 150 through the delivery tube 155 to the patient interface 160. In an embodiment, a liquid 145 contained in the chamber 120 can be heated by the heater 125 when the chamber 120 is mounted on the base 130 to heat and/or humidify the gases flowing through the chamber 120. In an embodiment, a controller 135 is adapted to control power delivered to the heater 125.

FIG. 2A illustrates an example embodiment of the medical device 140, and FIG. 2B illustrates an enlargement of a portion 210 of the medical device 140 illustrated in FIG. 2A. The base 130 can include a sensing arrangement 235. In an embodiment, the sensing arrangement 235 can be attached into an aperture 245 of a wall 240 of the base 130. In an embodiment, the base 130 includes a removable component 205 that includes the wall 240, such that the sensing arrangement 235 is attached to the removable component 205. The removable component 205 can be a cartridge that can removably connect to the base or base unit 130. In an embodiment, the sensing arrangement 235, or at least a sensing portion or probe of the sensing arrangement 235, can be positioned to be inserted into an aperture 225 on the inlet port 115 of the chamber 120 when the chamber 120 is mounted on the base 130.

A sensing arrangement 235, or at least a sensing portion thereof, may additionally or alternatively be positioned to be inserted into an aperture of the outlet port 150. Further, more than one aperture may be provided in the inlet port 115 and/or the outlet port 150, each being positioned and configured to receive at least one sensing arrangement 235 therethrough. For the avoidance of doubt, an aperture in the inlet port 115 and/or outlet port 150 may be configured to receive more than one sensing arrangement 235 therethrough and/or more than one sensing portion of the same sensing arrangement. As will be appreciated, particularly where sensing arrangements 235 or portions or probes thereof are provided in close proximity, such as at the inlet port 115, 150, it may be desirable to provide common components of or integration between the sensing arrangements 235. Thus, rather than there necessarily being a separate sensing arrangement 235 provided for each sensor supported by the sensing arrangement 235, the same sensing arrangement 235 may have more than one sensing portion or probe extending therefrom, each supporting a sensor. Further, each sensing arrangement 235 (or portion or probe) may include more than one sensor.

Additionally or alternatively, sensing arrangements 235 may interface with the gases elsewhere along their path, such as via aperture(s) provided in other positions on the chamber 120 (e.g. the main sidewall or the top), along one of the tubes used to convey gases between the gases source and the patient interface, the patient interface or cuff connectors used to sealingly connect components of the system together.

According to one embodiment, a respective at least one (preferably one or two) sensing arrangement 235 (or sensing portion or probe thereof) is arranged to be received through a corresponding at least one aperture in each of the inlet port 115 and the outlet port 150. According to one embodiment, a single sensing arrangement 235 (or sensing portion or probe thereof) is associated with the inlet port 115, preferably for measuring temperature, whereas two sensing arrangements 235 (or two sensing portions or probes of the same or different sensing arrangements 235) are associated with the outlet port, preferably for measuring temperature and flow. However, other sensor types may additionally or alternatively be used, dependent somewhat on the particular application. Some examples of these are listed hereinbelow.

In an embodiment, the sensing arrangement 235 is adapted to measure a property or characteristic of gases flowing through the inlet port 115 and to provide a signal representative of the measured property or characteristic to the controller 135. For example, the sensing arrangement 235 may provide a signal to the controller 135 that represents a temperature of gases or flow rate of gases flowing through the inlet port 115 past the sensing arrangement 235. In an embodiment, the controller 135 can use the measured temperature, at least in part, to determine an amount of power to deliver to the heater 125. As will be appreciated, the controller may be provided elsewhere with appropriate communicative couplings provided for the transfer of data. Further, control may be distributed with processing occurring using more than one controller, said controllers being co-located and/or spaced apart, again with known wired and/or wireless communicative couplings provided therebetween. The sensors may be used simply to record parameters sensed. Such data may be used, for example, provide information on use of the apparatus for patient compliance purposes. However, more preferably, the sensed parameters may be used in effecting control of the wider apparatus. For example, flow rate may be adjusted or heating applied by a heater of the chamber may be varied. Similarly, heating applied by a heatable delivery tube may additionally or alternatively be varied. Where other parameters are monitored such as constituents of gases delivered, actuators may be controlled to enable the composition of the gases to change. For example, a valve may be opened to enable additional oxygen to be fed into the gas stream.

To this end and by way of example only, the sensing arrangement may comprise any one or more of:

a thermistor, a thermocouple, a resistance temperature detector (RTD), thermopile for measuring temperature,
a thermistor, heated wire or element, Venturi, anemometer for measuring flow.
a transducer, diaphragm, strain gauge for measuring pressure,
a microphone or transducer for measuring noise,
a gas concentration and/or composition sensor (e.g. oxygen, helium, nitric oxide, carbon dioxide sensors),
a sensor adapted for systems in which additives, such as medicaments, are provided to the gases supplied to a patient e.g. using a nebulizer
a pH sensor,
an enthalpy sensor,
additional or alternative sensors as would be known to one skilled in the art.

Said sensors and/or said associated processing logic may be adapted to measure or derive absolute values of the parameters being monitored and/or changes therein and/or rates of change therein.

While component 205 is removable according to preferred embodiments, the invention is not limited to it being so. Rather, the component 205 may be fixedly or irremovably coupled to the base 130. Alternatively, the component 205 may be formed integrally with the base 130 such that component 205 is a constituent part of the base 130. Some degree of removability of component 205 is preferred since this enables the sensing components to be easily repaired or replaced without having to replace the entire base 130. Further, it can allow for different components 205 to be used for different applications. For example, some applications may involve different operational parameters (temperature, flow, pressure etc.) and the sensors used for each can then be tailored without having to replace the entire base unit 130. Further, for some applications, different numbers of sensors may be desirable, the removability again providing for easy adaptation of the system to a particular application. Further, component 205 may include processing logic for, at least in part, processing the data received from the sensors. Removability allows for adaptation of the logic for different applications by using different components 205 with different configurations (in terms of hardware (e.g. number and/or positions of sensors) and/or logic) although an alternative on the logic side would be to provide for some form of communicative coupling so that the logic could be manipulated without removing the component 205 from the heater base.

In some embodiments, the chamber 120 includes a seal 215 positioned in the aperture 225 on the inlet port 115. The seal 215 can include a base portion 230 adapted to prevent gases from escaping the chamber 120 through the aperture 225 when the sensing arrangement 235 is inserted into the aperture 225. In some embodiments, the seal 215 can include a cap portion 220 adapted to separate the sensing arrangement 235 from gases in the chamber 120 but still allow the sensing arrangement 235 to measure a characteristic of the gases through the cap portion 220. In some such embodiments, some or all of the cap portion 220 may be rigid. In some such embodiments, some or all of the cap portion 220 may be flexible; for example, the sensing arrangement 235 may cause the cap portion 220 to stretch when the sensing arrangement 235 is inserted into the aperture 225 and thus into the seal 215. In some embodiments, the seal 215 may include no cap portion 220, thus allowing the sensing arrangement 235 to directly contact gases in the chamber 120. The seal may be formed from silicone or any other suitable resilient polymer.

Figure 3:
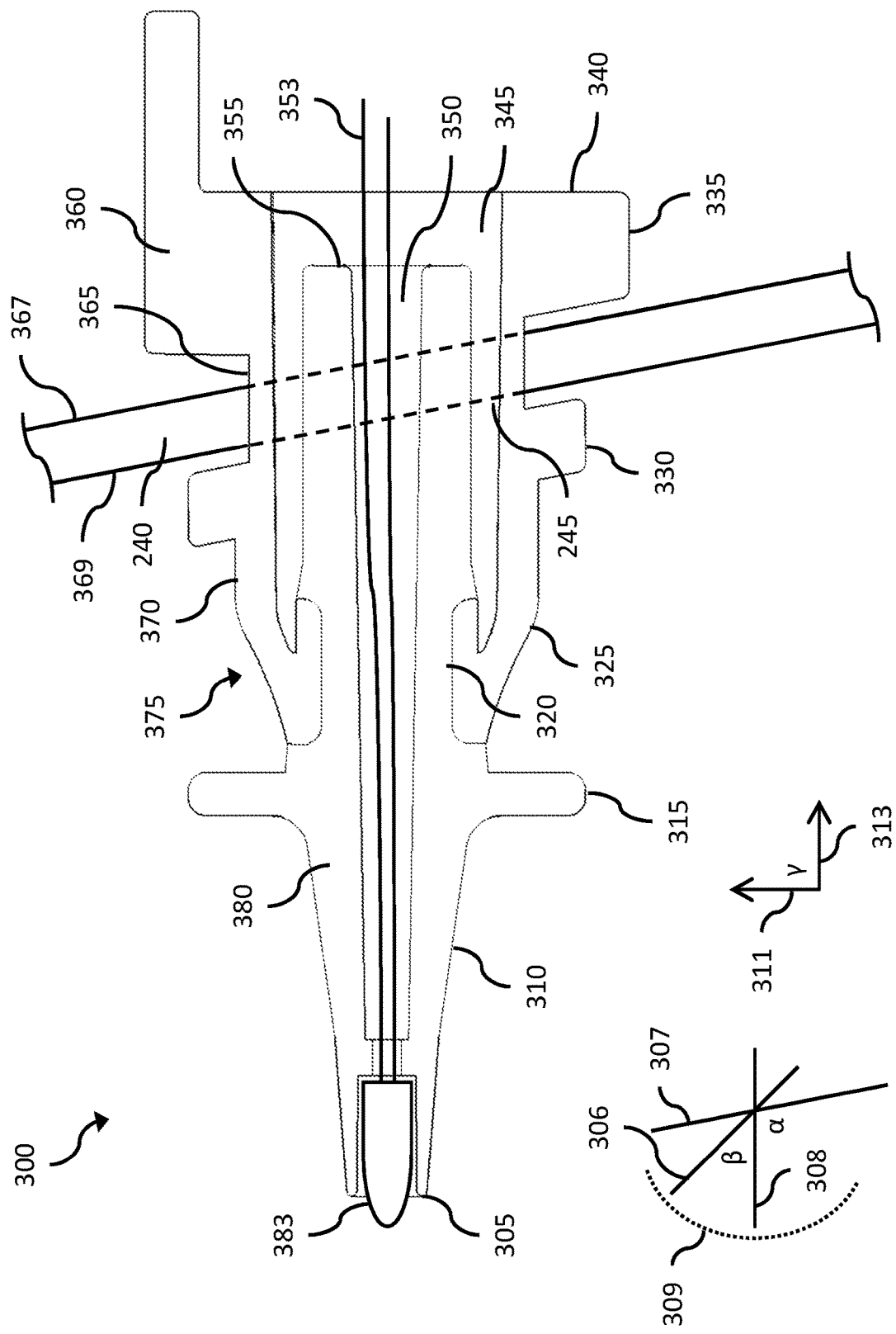
FIG. 3 illustrates a side cross-sectional view of an example embodiment of the sensing arrangement of FIG. 2B.
Figure 4:
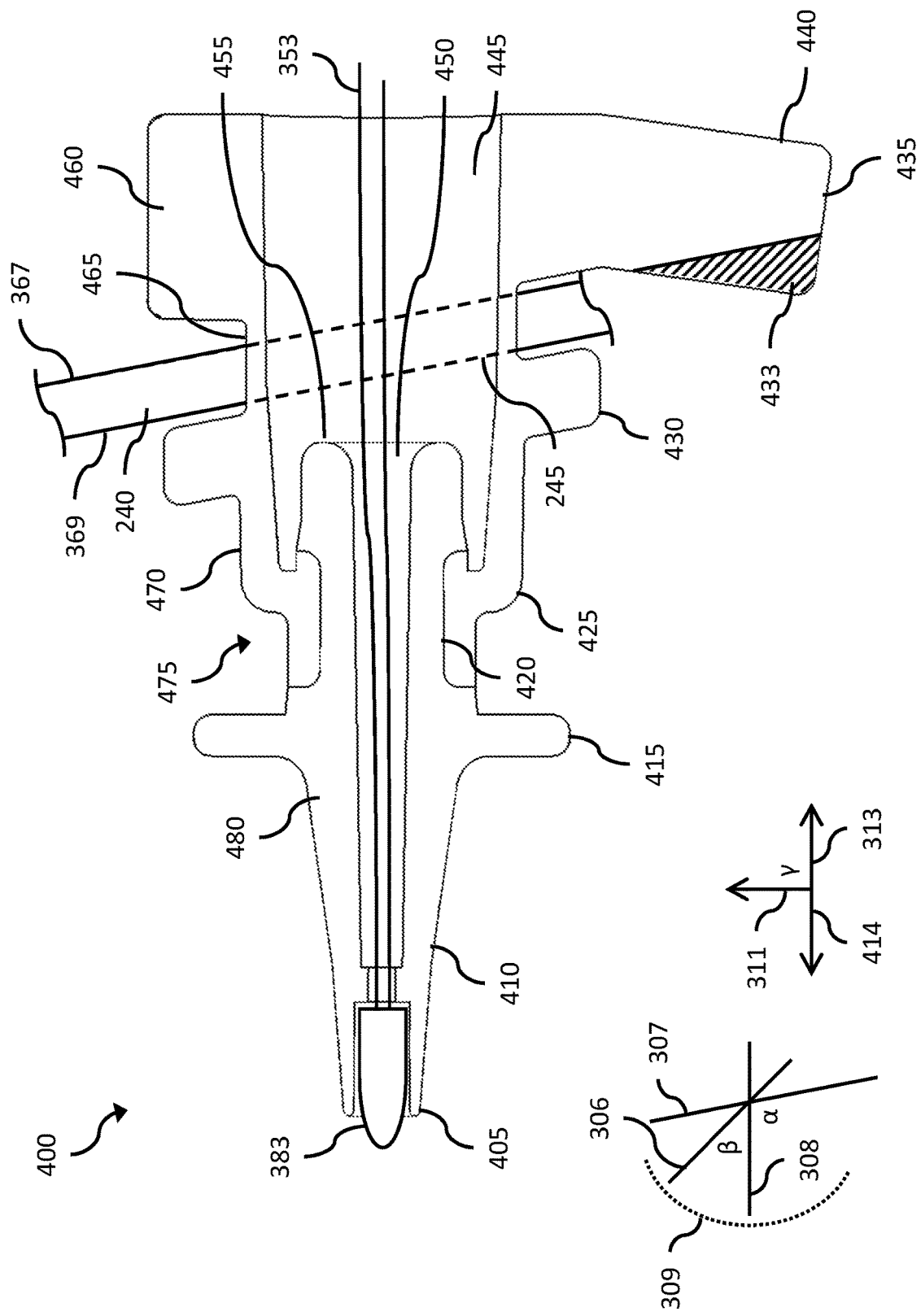
FIG. 4 illustrates a side cross-sectional view of an example embodiment of the sensing arrangement of FIG. 2B.

FIGS. 3 and 4 illustrate side cross-sectional views of a sensing arrangement 300 and a sensing arrangement 400, respectively, that are example embodiments of the sensing arrangement 235 with some similarities, as described. The sensing arrangement 300, 400 can include a housing 375, 475 that includes a rigid portion 380, 480 and a flexible portion 360, 460. The rigid portion 380, 480 can include a tip 305, 405 and a stem 355, 455. An exterior 310, 410 of the rigid portion 380, 480 can extend from the tip 305, 405 to the stem 355, 455. The flexible portion 360, 460 can include a collar region 325, 425 and a tail region 340, 440. An exterior 370, 470 of the flexible portion 360, 460 can extend from the collar region 325, 425 to the tail region 340, 440. The flexible portion 360, 460 can include a rear flange 335, 435 protruding from the exterior 370, 470 in the tail region 340, 440; a front flange 330, 430 protruding from the exterior 370, 470 between the collar region 325, 425 and the rear flange 335, 435; and a throat region 365, 465 of the exterior 370, 470 between the front flange 330, 430 and the rear flange 335, 435.

An interior 345, 445 of the flexible portion 360, 460 of the sensing arrangement 300, 400 can extend from the collar region 325, 425 to the tail region 340, 440. The collar region 325, 425 can be attached to an attachment region 320, 420 of the exterior 310, 410 of the rigid portion 380, 480 between the tip 305, 405 and the stem 355, 455. A passageway 350, 450 of the rigid portion 380, 480 can extend from the tip 305, 405 to the stem 355, 455. A sensing element 383 can be positioned at least partially within the passageway 350, 450 at the tip 305, 405. At least one wire 353 can be attached to the sensing element 383. The at least one wire 353 can extend from the sensing element 383 through the passageway 350, 450 to the stem 355, 455 and into the interior 345, 445 of the flexible portion 360, 460.

As described above with respect to the sensing arrangement 235, the sensing arrangement 300, 400 can be attached to or otherwise provided to or formed with the base 130 and/or the removable component 205. The throat region 365, 465 can be positioned within the aperture 245 of the wall 240, so as to position the front flange 330, 430 adjacent an outside 369 of the wall 240 and to position the rear flange 335, 435 adjacent an inside 367 of the wall 240. A sealing flange 315, 415 can protrude from the exterior 310, 410 of the rigid portion 380, 480 between the tip 305, 405 and the attachment region 320, 420. When the sensing arrangement 300, 400 is attached to the base 130, the sealing flange 315, 415 is adapted to contact the base portion 230 of the seal 215 when the chamber 120 is mounted on the base 130 (and thus when the sensing arrangement 300, 400 is inserted into the aperture 225 on the inlet port 115).

The collar region 325, 425 of the flexible portion 360, 460 of the sensing arrangement 300, 400 is adapted to allow an external force exerted against the rigid portion 380, 480 to cause the rigid portion 380, 480 to move away from a rest position in response to the external force and then return to the rest position in the absence of the external force. With respect to the plane of the cross-section illustrated in FIGS. 3 and 4, an example of a rest position can be represented by a line between the tip 305, 405 and the stem 355, 455 being parallel to a line segment 308 that has an angle α to a line segment 307 that is parallel to the wall 240.

Discussion follows on example vectors. These are for illustrative purposes only. The vectors in practice will vary somewhat as the chamber is installed onto or removed from the base. Further, tolerances may allow for the chamber to be in slightly different positions or orientations when in the rest state with the chamber operably installed on the base. Further still, the base and/or the chamber and/or the sensing arrangement and/or the removable portion may be configured differently, still embodying the invention but with different resultant vectors.

An example external force exerted against the rigid portion 380, 480 may have an inward component, which is a component of force in the direction of a vector 313 from the tip 305, 405 toward the stem 355, 455 that is parallel to the line segment 308. An inward component of force exerted against the rigid portion 380, 480 can cause the collar region 325, 425 to compress with a spring force in response to the inward component of force. When the inward component of force is exerted by the base portion 230 of the seal 215 against the sealing flange 315, 415—when the chamber 120 is being mounted on the base 130—a spring force produced in response by the collar region 325, 425 presses the sealing flange 315, 415 against the base portion 230 to hold the sensing element 383 in position inside the cap portion 220 of the seal 215 and, according to preferred embodiments, to cause the cap portion 220 to stretch.

An example external force exerted against the rigid portion 380, 480 may have a side component, which is a component of force in the direction of a vector 311 that has some non-zero angle β to the line segment 308. A side component of force exerted against the rigid portion 380, 480 can cause the collar region 325, 425 to flex, allowing the rigid portion 380, 480 to move so that the sensing element 383 moves in a direction similar to the side component of force—although not in the same direction, since the attachment of the sensing arrangement 300, 400 to the wall 240 at the throat region 365, 465 will cause the sensing element 383 to move following, for example, an arc 309 rather than a straight line.

With regard to FIG. 3, the stem 355 of the sensing arrangement 300 can be positioned within the interior 345 of the flexible portion 360 between a plane passing through the tail region 340 that is normal to the line segment 308 and a plane passing through the throat region 365 that is parallel to the line segment 307 when the sensing arrangement 300 is attached into the aperture 245 of the wall 240 and is at rest. In other words, when the sensing arrangement 300 is attached to the base 130, the rigid portion 380 extends through the aperture 245. A side component of force in the direction of the vector 311 exerted against the rigid portion 380 may cause the rigid portion 380 to move such that a line between the tip 305 and the stem 355 is parallel to, for example, a line segment 306 having an angle β to the line segment 308. For a sufficiently large angle β, the rigid portion 380 may pinch the flexible portion 360 in the throat region 365 against the wall 240, which could cause the flexible portion 360 to weaken or tear.

With regard to FIG. 4, the stem 455 of the sensing arrangement 400 can be positioned within the interior 445 of the flexible portion 460 between a plane passing through the collar region 425 that is normal to the line segment 308 and a plane passing through the throat region 465 that is parallel to the line segment 307 when the sensing arrangement 400 is attached into the aperture 245 of the wall 240 and is at rest. In other words, when the sensing arrangement 400 is attached to the base 130 (including via the removable component 205), the rigid portion 480 does not extend through the aperture 245. The stem 455 does not extend into the aperture 245. A side component of force in the direction of the vector 313 exerted against the rigid portion 480 may cause the rigid portion 480 to move such that a line between the tip 405 and the stem 455 is parallel to, for example, the line segment 306 having the angle β to the line segment 308.

Even for a large angle β, the rigid portion 480 will not pinch the flexible portion 460 in the throat region 465 against the wall 240. The stem 455 not inserting into the aperture is advantageous because it reduces the likelihood of the wall 240 acting on the stem if the sensing arrangement is bent during use. This reduces bending stresses on the stem and thus reduces the chance of the stem from breaking and thus reducing the chance of the wire 353 breaking due to the bending stresses acting through the stem. Still with reference to FIG. 4, the collar portion 425 comprises a shorter radius of an arc portion adjacent the connection portion 420. The shorter radius promotes a rolling behavior of the resilient or flexible portion 460. The flexible portion 460, by being resiliently deformable, acts as a spring or resilient member as the collar portion 425 is moved relative to other parts of the sensing arrangement. The collar portion 425, and the curved section of the collar portion rolls over the attachment region 420 as the rigid portion 480 is pushed inward toward the aperture 245. The thickness of the flexible portion 460 is greater at the collar region 425 and thinner at the throat region 465. The thicker flexible portion 465 at the collar region 425 assists in creating the rolling motion as the sensor or sensing arrangement is compressed during operation. The collar region 425 rolls over the attachment region 420 as the rigid portion moves axially in use. The thickness at the collar region can be between 0.5 mm and 1.5 mm, more preferably between 0.8 mm and 1.25 mm, more preferably between 0.86 mm and 1.21 mm. According to some embodiments, the thickness at the collar region can be between 1.05 mm and 1.25 mm. The internal radius of the curved section of the collar 425 may be between 0.1 mm and 1 mm, more preferably between 0.3 mm and 0.8 mm and more preferably still between 0.4 mm and 0.75 mm. Due to the shorter radius of the collar portion and the increased thickness in the collar region, a more constant spring force is achieved, a rolling action is achieved and reduced buckling is achieved as the sensing arrangement (i.e. the rigid portion) is compressed in use. The spring force may be between 0.1N and 15N, more preferably between 0.1N and 10N, more preferably still between 0.3N and 5N, over the force profile applied to the sensing arrangement. According to some embodiments, the spring force is between 0.5N and 1.5N over the force profile applied to the sensing arrangement.

The rear flange 435 is shown in FIG. 4 in a relaxed configuration, in other words with no external forces exerted against it. A portion 433 (shown shaded in FIG. 4) of the rear flange 435 is positioned such that when the sensing arrangement 400 is attached into the aperture 245 of the wall 240, the portion 433 would occupy the same space as the wall 240 unless the rear flange 435 bends to move the portion 433 out of the way of the wall 240. Bending causes the rear flange 435 to exert force against the wall 240; for example, an outward component of force exerted by the rear flange 435 against the wall 240 can be in the direction of a vector 414. The outward component of force can help to hold the sensing arrangement 400 in position against the wall 240. It can also assist in moving, the chamber for example, away when desired since this force acts thereon (by the wall thereof being received in the recesses 610, 710—see FIGS. 6-9).

Figure 5:
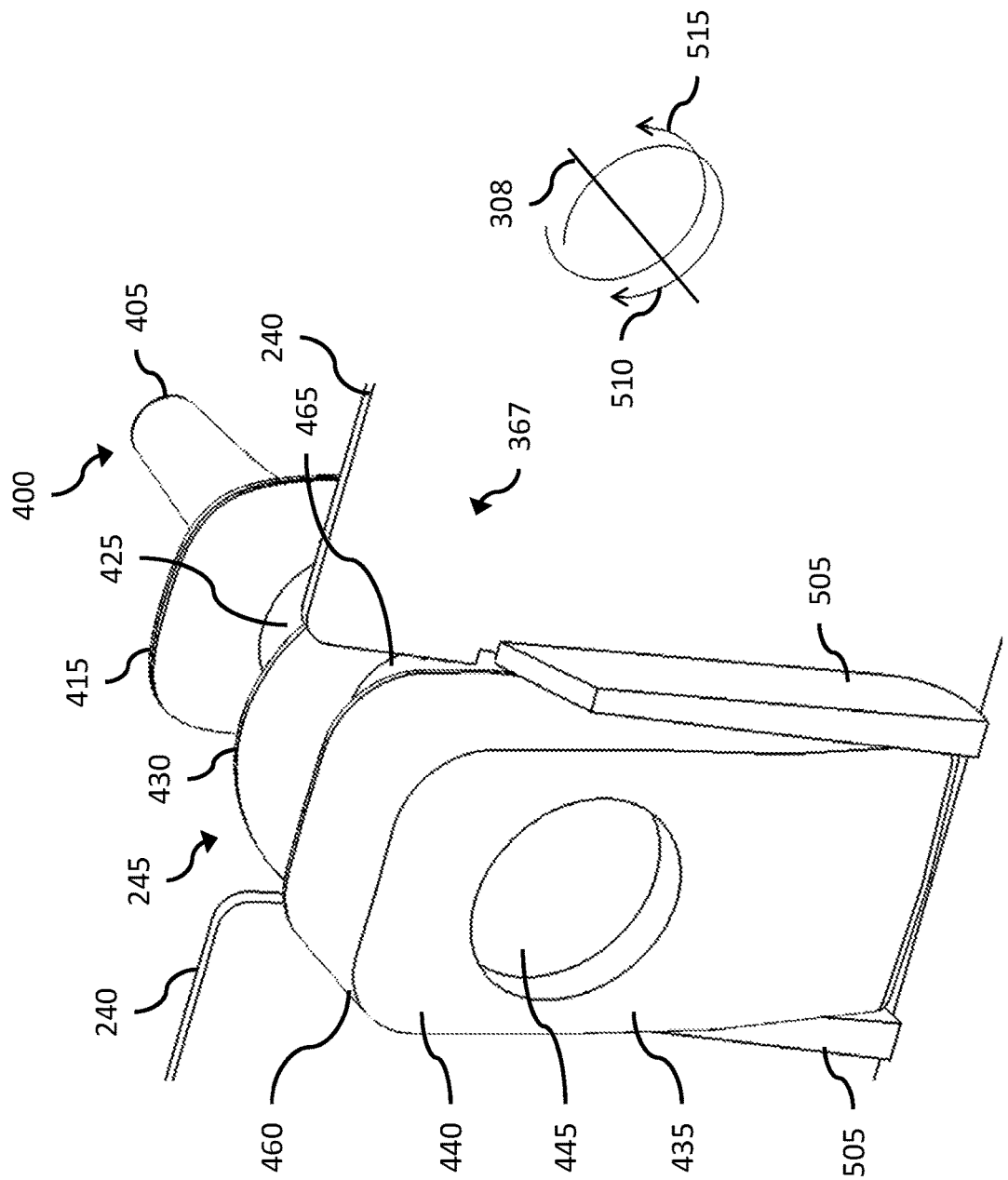
FIG. 5 illustrates a cut-away rear view of the sensing arrangement of FIG. 4 attached to the medical device of FIG. 2A.

FIG. 5 illustrates a cut-away view of the wall 240 from inside the removable component 205, showing the sensing arrangement 400 attached into the aperture 245 of the wall 240. The view shown in FIG. 5 could alternatively be of an aperture in the wall of the base where the removable component 205 is formed by the base 130. The rear flange 435 is positioned to exert force against the wall 240, as described above. A pair of baffles 505 protrude from the inside 367 of the wall 240 on either side of the aperture 245 such that the rear flange 435 is positioned between the pair of baffles 505 when the sensing arrangement 400 is attached into the aperture 245. The pair of baffles 505 help to prevent rotational movement of the sensing arrangement 400 around the axis of the line segment 308 by blocking motion of the rear flange 435 in directions 510 and 515 that lie in a plane normal to the line segment 308. The rear flange 435 may have a height that is more than three quarters the height of the baffles 505. The height of the rear flange 435 being greater than three quarters the height of the baffles 505 reduces the chances of the rear flange 435 riding up and over the baffles 505 and allowing rotation of the sensing arrangement. Lesser heights may also suffice, particularly depending on the resiliency and/or stiffness of the material forming the flexible portion. Essentially, the stiffer or more resilient the material, the more the height in the baffles can be reduced. Further, the stiffness of the flexible portion may be varied so as to be stiffer in some parts, such as at the flange 435. For example, different curing parameters may be used for different parts of the flexible portion and/or a rigid or more rigid member may be incorporated into or joined to a portion of the flexible member. For example, a plate-like member could be embedded in or joined to the flange 435 with the result that baffles 505 may have a lesser height, FIGS. 6 and 7 illustrate side cross-sectional views of a seal 600 and a seal 700, respectively, that are example embodiments of the seal 215 with some similarities, as described, and side cross-sectional views of a portion of a sensing arrangement 660 that is an example embodiment of the sensing arrangement 235. The seal 600, 700 can include a base portion 605, 705 and a cap portion 615, 715 that are example embodiments of the base portion 230 and the cap portion 220, respectively, that are described above. The base portion 605, 705 can be joined to the cap portion 615, 715 by an inset region 610, 710. The cap portion 615, 715 can include a target region 630, 730, a shoulder region 640, 740, and a side region 620, 720. The shoulder region 640, 740 can surround the target region 630, 730 and join the target region 630, 730 to the side region 620, 720.

The target region 630, 730 can include an inner target surface 635, 735 having a substantially flat profile that is parallel to a plane containing a vector 633, 733. The side region 620, 720 can include an inner side surface 625, 725 having a substantially flat profile that is parallel to a plane containing a vector 631, 731 that has an angle δ, θ to the vector 633, 733. The shoulder region 640, 740 can include an inner shoulder surface 645, 745 having a curved profile that transitions from the plane of the inner target surface 635, 735 to the plane of the inner side surface 625, 725 through the angle δ, θ. A width ω, ψ can define an extent of the inner target surface 635, 735 that is substantially flat and parallel to the plane containing the vector 633, 733. Within the width ω, ψ, the target region 630, 730 can have a substantially uniform thickness κ, λ.

The sensing arrangement 660, more particularly the sensing portion or probe thereof, comprises a sealing flange 665, a rigid portion 655, and a sensing element 650, each having similar properties to the sealing flange 315, 415, the rigid portion 380, 480, and the sensing element 383, respectively, of the sensing arrangement 300, 400. The sealing flange 665 is adapted to contact the base portion 605, 705 and the sensing element 650 is adapted to contact the cap portion 615, 715 when the sensing arrangement 660 is attached to the base 130 and the chamber 120 is mounted on the base 130, as previously described. In an embodiment, the sensing element 650 is adapted to contact the inner target surface 635, 735 of the cap portion 615, 715 within the width ω, ψ.

In an embodiment, the sensing arrangement 660 (as well as other sensing arrangements described herein) can be calibrated, and the controller 135 can be configured, such that the sensing arrangement 660 provides a signal to the controller 135 that accurately represents a desired transform of a measurement made by the sensing arrangement 660 through the substantially uniform thickness κ, λ of the target region 630, 730. For example, the sensing arrangement 660 can measure a temperature of 50.0° C. through the target region 630, 730 of gases in the chamber 120 and provide a signal to the controller 135 that the controller 135 interprets as 50.0±0.1° C. If the sensing element 650 does not contact the inner target surface 635, 735—for example, if the sensing element 650 instead contacts the inner shoulder surface 645, 745—the sensing arrangement 660 may provide a signal to the controller 135 that does not accurately represent a desired transform of the measurement made by the sensing arrangement 660.

The shoulder region 640, 740 may have a thickness different from the substantially uniform thickness κ, λ of the target region 630, 730, which may cause a measurement made by the sensing arrangement 660 through the shoulder region 640, 740 to be inaccurate. Thus, it is preferred that the sensing element 650 contact the inner target surface 635, 735 and not the inner shoulder surface 645, 745. A width π, ρ can define an extent of a projection of the inner shoulder surface 645, 745 onto the plane containing the vector 633, 733, the width π, ρ being inclusive of the width ω, ψ of the inner target surface 635, 735. In other words, the π, ρ represents an inner diameter of the cap portion 615, 715. The inner shoulder surface 645, 745 itself occupies an annular space (in projection onto the plane containing the vector 633, 733) around the inner target surface 635, 735, the annular space having a ring width (that is, a difference in diameter between concentric circles) of (π−ω)/2, (ρ−ψ)/2.

In embodiments of the seal 600 and the seal 700 where the cap portion 615 and the cap portion 715 share a common inner diameter, such that π=ρ, and the inner target surface 735 is wider than the inner target surface 635, such that ψ>ω, then (ρ−ψ)/2<(π−ω)/2, making the ring width of the inner shoulder surface 745 narrower than the ring width of the inner shoulder surface 645. For example, in embodiments of the seal 600 and the seal 700 with π=ρ=3.5 mm, if ψ=3.25 mm and ω=1.5 mm, then the ring width of the inner shoulder surface 645 is (π−ω)/2=1.0 mm and the ring width of the inner shoulder surface 745 is (ρ−ψ)/2=0.13 mm. Considered another way, in this example, the width of the inner target surface 635 represents ω/π=43% of the width of the combination of the inner target surface 635 and the inner shoulder surface 645, whereas the width of the inner target surface 735 represents ψ/ρ=93% of the width of the combination of the inner target surface 735 and the inner shoulder surface 745. The increased inner target surface region provides a greater area for the sensor tip to engage an optimal sensing region of the seal.

According to some embodiments, widths π and ρ are greater than 0 mm and less than or equal to 20 mm more preferably between 2 mm and 15 mm and more preferably between 4 mm and 10 mm. Widths ω and ψ may be less than 15 mm, more preferably less than 10 mm and more preferably less than 8 mm. Thicknesses κ and λ may be less than 2.5 mm, preferably less than 2 mm and more preferably less than 1.5 mm.

Figure 9:
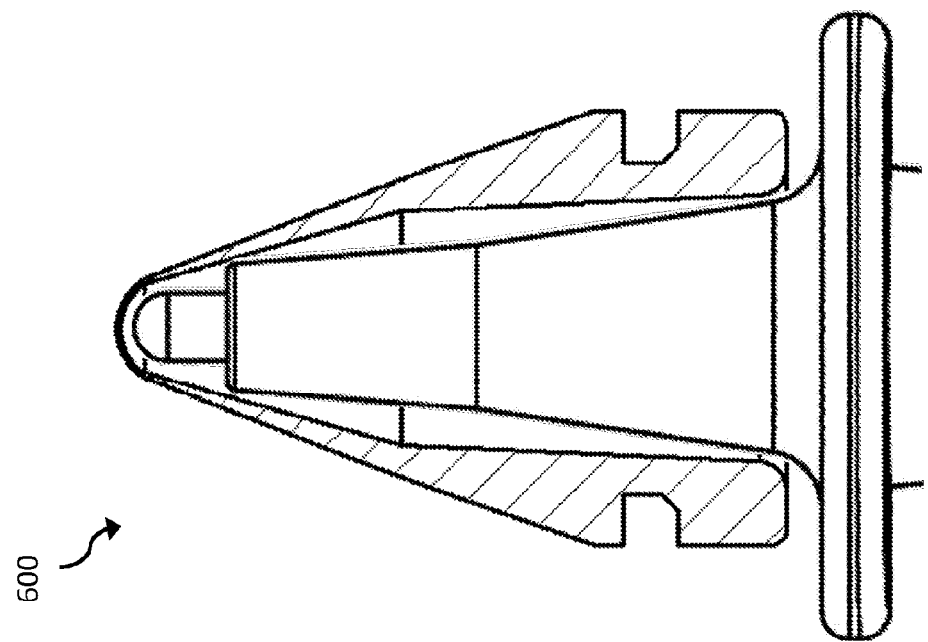
FIG. 9 illustrates a side cross-sectional view of the seal of FIG. 8 in a second, operative position or state.
Figure 8:
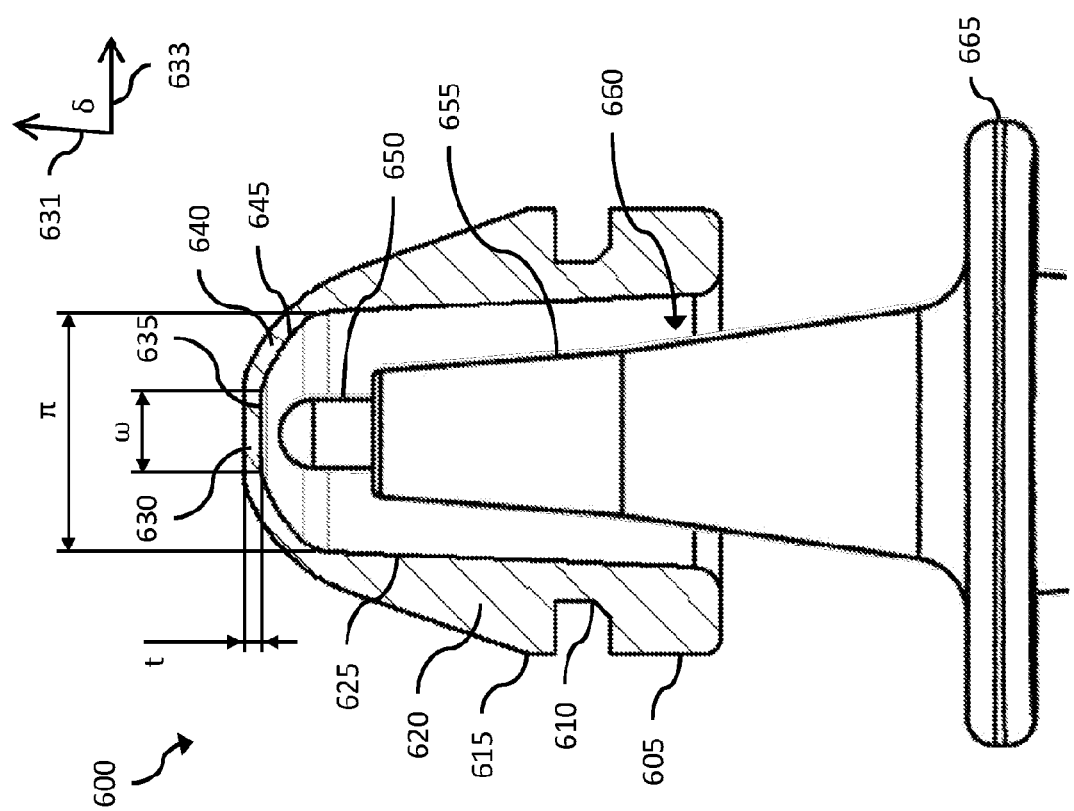
FIG. 8 illustrates a side cross-sectional view of an example embodiment of the seal of FIG. 2B with the seal in a first, rest position or state.

FIGS. 8 and 9 show an alternative embodiment. In FIG. 8, the sensing element 650 has been partially inserted into the seal 600. In this position, the seal is at rest i.e. not subject to force by the housing from the tip contacting the target region but held in position with the inset region received inside the aperture defining the port and the base portion and the cap portion of the seal on either side of the wall defining the aperture.

FIG. 9 shows the sensing portion 650 more fully inserted into the seal 600, into an operative position for sensing, a configuration which would result, for example, from the chamber being fully, or near fully, operably installed on the base. According to the embodiment of FIGS. 8 and 9, at least a portion of the seal 600 is elastically deformable such that as the sensing element 650 is inserted, a portion of the wall forming the seal thins. Preferably, said at least a portion that is elastically deformable comprises at least the target portion 635. Since the sensing element is configured to sense in the target portion 635, the thinning of the wall in that region enables more accurate measurements to be taken while still isolating and protecting the sensing element from the environment to be sensed. However, at the early stages of insertion, where movement is less constricted or controlled, the wall is relatively thick, better preventing tearing etc.

Additional or alternative parts of the seal may be elastically deformable. More preferably, the seal may be integrally moulded from a single, elastically deformable material, such as a silicone or any other suitable resilient polymer, such that the entire seal is resiliently deformable.

In the at rest or unstretched configuration shown in FIG. 8, the thickness t in the target region may be less than 2.5 mm, preferably less than 2 mm and more preferably less than 1.5 mm and reduce to below 1.5 mm, preferably less than 1 mm or 0.5 mm when stretched as shown in FIG. 9. Similarly, in the at rest or unstretched configuration shown in FIG. 8, the length of the interior passageway of the seal (i.e. from the underside or inside of the target region to the bottom of the base portion) id less than 50 mm in the at rest position in FIG. 8, preferably less than 30 mm and more preferably less than 15 mm. This length may increase to up to 50 mm in the stretched configuration shown in FIG. 9, preferably up 35 mm and more preferably up 20 mm.

The foregoing description of the invention includes preferred forms thereof. Modifications may be made thereto without departing from the scope of the invention. To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

What is claimed is:

1. A sensing arrangement for a medical device comprising:
 a housing including:
  a rigid portion including a tip at a first end and a stem at an opposite, second end;
  a flexible portion including:
   a collar region and a tail region, a rear flange protruding from the flexible portion in the tail region, a front flange protruding from the flexible portion between the collar region and the rear flange, a throat region being between the front flange and the rear flange, the collar region being attached to an exterior of the rigid portion between the tip and the stem; and wherein the stem is positioned within the flexible portion between a first plane passing through the tail region and a second plane passing through the throat region.

2. A sensing arrangement for a medical device comprising:
a housing including:
a rigid portion including a tip at a first end and a stem at an opposite, second end;
a flexible portion including:
a collar region and a tail region, a rear flange protruding from the flexible portion in the tail region, a front flange protruding from the flexible portion between the collar region and the rear flange, a throat region being between the front flange and the rear flange, the collar region being attached to an exterior of the rigid portion between the tip and the stem; and
wherein the stem is positioned within the flexible portion between a first plane passing through the collar region and a second plane passing through the throat region.

3. The sensing arrangement of claim 2 comprising a passageway of the rigid portion extending from the tip to the stem, a sensing element positioned at least partially within the passageway at the tip, and at least one wire attached to the sensing element and extending through the passageway to the stem and into an interior of the flexible portion.

4. The sensing arrangement of claim 2, wherein the collar region is configured to roll over a portion of the rigid portion as the rigid portion moves axially.

5. The sensing arrangement of claim 2, wherein the collar region comprises a curved region that is configured to roll over an attachment region, the attachment region being a region where the flexible portion connects to the rigid portion.

6. The sensing arrangement of claim 2, further comprising a seal, the seal engaging the housing in use to protect the housing and a sensor associated with the housing.

7. The sensing arrangement of claim 6, wherein the seal have a target region that contacts the sensor and a width of the target region is 90% or more of the width of an opening in the seal, wherein the opening is configured to receive the housing and the sensor within the opening.

8. The sensing arrangement of any of claim 7, wherein the seal comprises a cap portion, said target region forming at least part of the cap portion, the cap portion comprising at least a portion configured to stretch when the housing and sensor within it is received therein.

9. The sensing arrangement of claim 7, wherein the housing comprises a sealing flange provided between the tip and the collar region, the sealing flange for sealingly mating with the seal at an end thereof distal from the target region.

10. The sensing arrangement of claim 9, wherein the sealing flange protrudes from the exterior of the rigid portion.

11. The sensing arrangement of claim 9, wherein the seal defines an internal passageway that is closed at a first end, said first end being formed at least in part by the target region, wherein, at rest, a length of said internal passageway is less than a length of the housing between the tip and the sealing flange.

12. The sensing arrangement of claim 11 wherein the seal is configured to stretch such that a second end of the seal contacts the sealing flange when in an operative position with the housing received inside the internal passageway, the second end being distal from the first end and defining an opening into the internal passageway.

13. The sensing arrangement of claim 2, wherein at least part of the flexible portion is resiliently deformable and acts as a spring or resilient member such that the rigid portion is urged towards a rest position.

14. A removable component for a medical device, the removable component comprising: a sensing arrangement according to claim 2, and a wall having an aperture therein, the aperture being configured to receive the sensing arrangement therein.

15. The removable component of claim 14, wherein the aperture is dimensioned to receive the housing such that the wall is positioned between the rear flange and the front flange.

16. The removable component of claim 14, wherein the removable component is configured to permanently or removably couple to said medical device by a structural coupling configured to fix the removable component in position relative to the medical device, or an electrical or communicative coupling configured to enable: signals from sensor(s) of the sensing arrangement, or data derived therefrom, to be communicated to the medical device, or components of the sensing arrangement to be electrically powered by the medical device, or the structural coupling and the electrical or communicative coupling, or a combination thereof.

17. A medical device comprising a sensing arrangement according to claim 2, the medical device further comprising a wall having an aperture therein, wherein the aperture is dimensioned to receive the housing such that the wall is positioned between the rear flange and the front flange.

18. The medical device of claim 17, comprising a removable component, wherein the wall is part of the removable component.

19. The medical device of claim 17, comprising a heater base, the heater base being configured to receive a liquid chamber and heat contents thereof.

20. The medical device of claim 19, wherein, upon engagement of the liquid chamber with the heater base, at least a portion of the housing of the sensing arrangement is received in an aperture in the liquid chamber.

21. The medical device of claim 18, wherein the wall of the removable component includes a pair of baffles that are spaced apart from each other, wherein the rear flange is configured to be received between the pair of baffles to prevent rotation of the rear flange.

22. The medical device of claim 21, wherein the rear flange has a height that is three quarters or more than a height of one of the pair of baffles.

23. The medical device of claim 18, wherein the removable component is configured to couple to the medical device via an electrical or communicative coupling configured to enable: signals from sensor(s) of the sensing arrangement, or data derived therefrom, to be communicated to the medical device, or components of the sensing arrangement to be electrically powered by the medical device, or a combination thereof.

* * * * *

UNITED STATES PATENT AND TRADEMARK OFFICE
CERTIFICATE OF CORRECTION

| | |
|---|---|
| PATENT NO. | : 11,351,332 B2 |
| APPLICATION NO. | : 16/466263 |
| DATED | : June 7, 2022 |
| INVENTOR(S) | : Joshua Peter McIntyre et al. |

It is certified that error appears in the above-identified patent and that said Letters Patent is hereby corrected as shown below:

In the Claims

Column 15, Line 38, Claim 7, delete "have" and insert --has--.

Column 15, Line 42, Claim 8, delete "of any of claim" and insert --of claim--.

Signed and Sealed this
Twenty-third Day of August, 2022

Katherine Kelly Vidal
*Director of the United States Patent and Trademark Office*